(12) United States Patent
Artzi et al.

(10) Patent No.: US 9,707,313 B2
(45) Date of Patent: *Jul. 18, 2017

(54) BIOCOMPATIBLE ADHESIVE MATERIALS AND METHODS

(71) Applicant: Massachusetts Institute of Technology, Cambridge, MA (US)

(72) Inventors: Natalie Artzi, Brookline, MA (US); Elazer R. Edelman, Brookline, MA (US); Nuria Oliva Jorge, Barcelona (ES); Maria Carcole Solanes, Barcelona (ES)

(73) Assignee: Massachusetts Institute of Technology, Cambridge, MA (US)

( * ) Notice: Subject to any disclaimer, the term of this patent is extended or adjusted under 35 U.S.C. 154(b) by 167 days.

This patent is subject to a terminal disclaimer.

(21) Appl. No.: 14/446,805

(22) Filed: Jul. 30, 2014

(65) Prior Publication Data

US 2014/0341838 A1 Nov. 20, 2014

Related U.S. Application Data

(62) Division of application No. 13/446,712, filed on Apr. 13, 2012, now Pat. No. 8,802,072.

(60) Provisional application No. 61/474,984, filed on Apr. 13, 2011.

(51) Int. Cl.
| | |
|---|---|
| A61K 31/74 | (2006.01) |
| A61M 37/00 | (2006.01) |
| A61K 31/00 | (2006.01) |
| A61K 47/48 | (2006.01) |
| A61L 24/04 | (2006.01) |
| A61L 24/08 | (2006.01) |
| A61L 24/00 | (2006.01) |
| A61M 5/19 | (2006.01) |
| A61M 5/315 | (2006.01) |

(52) U.S. Cl.
CPC ......... *A61L 24/043* (2013.01); *A61L 24/0005* (2013.01); *A61L 24/0015* (2013.01); *A61L 24/08* (2013.01); *A61M 5/19* (2013.01); *A61M 5/31596* (2013.01)

(58) Field of Classification Search
CPC .................. A61M 5/31596; A61L 24/043
USPC .................. 424/78.02, 78.08, 78.17; 604/82
See application file for complete search history.

(56) References Cited

U.S. PATENT DOCUMENTS

| | | | |
|---|---|---|---|
| 4,768,523 | A | 9/1988 | Cahalan et al. |
| 5,306,504 | A | 4/1994 | Lorenz |
| 7,910,129 | B2 | 3/2011 | Kennedy et al. |
| 2004/0131582 | A1 | 7/2004 | Grinstaff |
| 2005/0238692 | A1 | 10/2005 | Hughes |
| 2006/0078536 | A1 | 4/2006 | Kodokian et al. |
| 2006/0079599 | A1 | 4/2006 | Arthur |
| 2011/0250257 | A1 | 10/2011 | Arthur et al. |
| 2012/0148523 | A1 | 6/2012 | Lu et al. |

OTHER PUBLICATIONS

Japanese Office Action for JP Application No. 2014-505357 mailed Jan. 25, 2016 (English translation) (7 pages).
Artzi et al., "Aldehyde-Amine Chemistry Enables Modulated Biosealants with Tissue-Specific Adhesion," Advanced Materials, 2009, pp. 3399-3403, vol. 21.
Artzi et al., "Characterization of Star Adhesive Sealants Based on PEG/Dextran Hydrogels," Macromol. Biosci., 2009, DOI: 10.1002/mabi.200800355, vol. 9.
Bhatia, et al., "Interactions of Polysaccharide-Based Tissue Adhesives with Clinically Relevant Fibroblast and Macrophage Cell Lines," Biotechnology Letters, 2007, pp. 1645-1649, vol. 29, No. 11. (Abstract Only).
Dong et al., "Effects of Polyamidoamine (PAMAM) Dendrimers on the Nasal Absorption of Poorly Absorbable Drugs in Rats," International Journal of Pharmaceutics, 2010, pp. 244-252, vol. 393.
Kumar et al., "Dendrimer: A novel Polymer for Drug Delivery," JITPS, 2010, pp. 252-269, vol. 1, No. 6.
PAMAM Dendrimers, www.dendritech.com/pamam.html, 2010.
The JEFFAMINE Polyetheramines, Huntsman Corp., 2007.
Shazly et al., "Viscoelastic Adhesive Mechanics of Aldehyde-Mediated Soft Tissue Sealants," Biomaterials, 2008, pp. 4584-4591, vol. 29.
Shrivastava et al., "Polyamidoamine Dendrimer and Dextran Conjugates: Preparation, Characterization, and in vitro and in vivo Evaluation," Chemical Papers, 2010, pp. 592-601, vol. 64, No. 5.
PCT International Search Report for PCT/US2012/033604 mailed Sep. 19, 2012.
Berdahl et al., "Comparison of Sutures and Dendritic Polymer Adhesives for Corneal Laceraction Repair in an in vivo Chicken Model," Archives of Ophthalmology, 2009, vol. 127, pp. 442-447.
Wang et al., "Fluorescence and Aggregation Behavior of Poly(amidoamine)Dendrimers Peripherally Modified with Aromatic Chromophores: the Effect of Dendritic Architectures," Journal of the American Chemical Society, 2004, vol. 126, pp. 15180-15194.
Jacchetti et al., "Biomimetic Poly(amidoamine) Hydrogels as Synthetic Materials for Cell Culture," Journal of Nanobiotechnology, 2008, vol. 6, p. 14.

(Continued)

*Primary Examiner* — Dennis J Parad

(74) *Attorney, Agent, or Firm* — Eversheds Sutherland (US) LLP

(57) ABSTRACT

Biocompatible adhesive materials, such as for use with biological tissues and/or medical implants, are provided, as well as methods and kits for making and using the biocompatible adhesive materials. The biocompatible adhesive materials include a dendrimer component and a polymer component, and may be tailored for specific tissue types and conditions.

11 Claims, 19 Drawing Sheets

(56) References Cited

OTHER PUBLICATIONS

Ferruti et al., "Novel Poly(amido-amine)-Based Hydrogels as Scaffolds for Tissue Engineering," Macromolecular Bioscience, 2005, vol. 5, pp. 613-622.
Agarwal et al., "Dextran Conjugated Dendritic Nanoconstructs as Potential Vectors for Anti-Cancer Agent," Biomaterials, 2009, vol. 30, pp. 3588-3596.
Wang et al., "Synthesis and Application to Carbohydrate-Containing Polymers," Chemistry of Materials, 2002, vol. 14, pp. 3232-3244.
Shi et al., "Comprehensive Characterization of Surface-Functionalized Poly(amidoamine) Dendrimers with Acetamide, Hydroxyl, and Carboxyl Groups," Colloids and Surfaces A: Physicochemical and Engineering Aspects, 2005, vol. 272, No. 1, pp. 139-150.

BIOCOMPATIBLE ADHESIVE MATERIALS AND METHODS

CROSS REFERENCE TO RELATED APPLICATIONS

This application is a division of U.S. patent application Ser. No. 13/446,712, filed Apr. 13, 2012, which claims priority to U.S. Provisional Patent Application No. 61/474,984, filed Apr. 13, 2011. The contents of U.S. patent application Ser. No. 13/446,712 and U.S. Provisional Patent Application No. 61/474,984 are incorporated herein by reference.

FIELD OF THE INVENTION

This disclosure relates to biocompatible adhesive materials, such as for use with biological tissues and/or medical implants, as well as methods and kits for making and using the biocompatible adhesive materials.

BACKGROUND

A number of tissue adhesives have been used in various medical procedures and applications, including topical wound closure, supplementing or replacing surgical sutures or staples, adhesion of synthetic materials to biological tissues, and drug delivery. A number of known tissue adhesives, however, are unsuitable for many applications, for example, due to toxic degradation products, slow curing, poor mechanical strength, and other drawbacks.

Several varieties of hydrogel adhesives have been developed, which are nontoxic and have improved properties. These hydrogels are generally formed by reacting a component having nucleophilic groups with a component having electrophilic groups that react to form a crosslinked network. However, these hydrogels typically dissolve too quickly, lack sufficient adhesion, or have insufficient mechanical strength.

Therefore, it would be desirable to provide improved adhesive formulations that overcome one or more of the above-described disadvantages.

SUMMARY

In one aspect, compositions and methods are provided for adhering, sealing, or treating one or more biological tissues. The method may include combining a polymer component and a dendrimer component in any manner to form an adhesive formulation, and contacting one or more biological tissues with the adhesive formulation. In embodiments, the polymer component comprises a polymer having one or more aldehyde groups. In embodiments, the dendrimer component comprises a dendrimer having at least 2 arms or branches with one or more surface groups. In certain embodiments, less than 75% of the surface groups comprise at least one primary or secondary amine. In some embodiments, the adhesive formulations are used in a method for treating, adhering, or sealing a biological tissue, the method comprising (1) providing a first solution comprising a polymer component, wherein the polymer component comprises a polymer having one or more aldehyde groups, (2) providing a second solution comprising a dendrimer component, wherein the dendrimer component comprises a dendrimer having at least 2 branches with one or more surface groups, wherein less than 75% of the surface groups comprise at least one primary or secondary amine, (3) combining the first and second solutions together to produce an adhesive formulation and contacting one or more biological tissues with the adhesive formulation, and (4) allowing the adhesive formulation to cure.

In another aspect, kits are provided for making and delivering an adhesive composition. The kit may include a first part that comprises a polymer component and a second part that comprises a dendrimer component. The polymer component may comprise a polymer having one or more aldehyde groups. The dendrimer component may comprise a dendrimer having at least 2 arms or branches with one or more surface groups. In certain embodiments, less than 75% of the surface groups comprise at least one primary or secondary amine. The kit may include means for mixing the first and second parts together.

DETAILED DESCRIPTION

Figure 1:
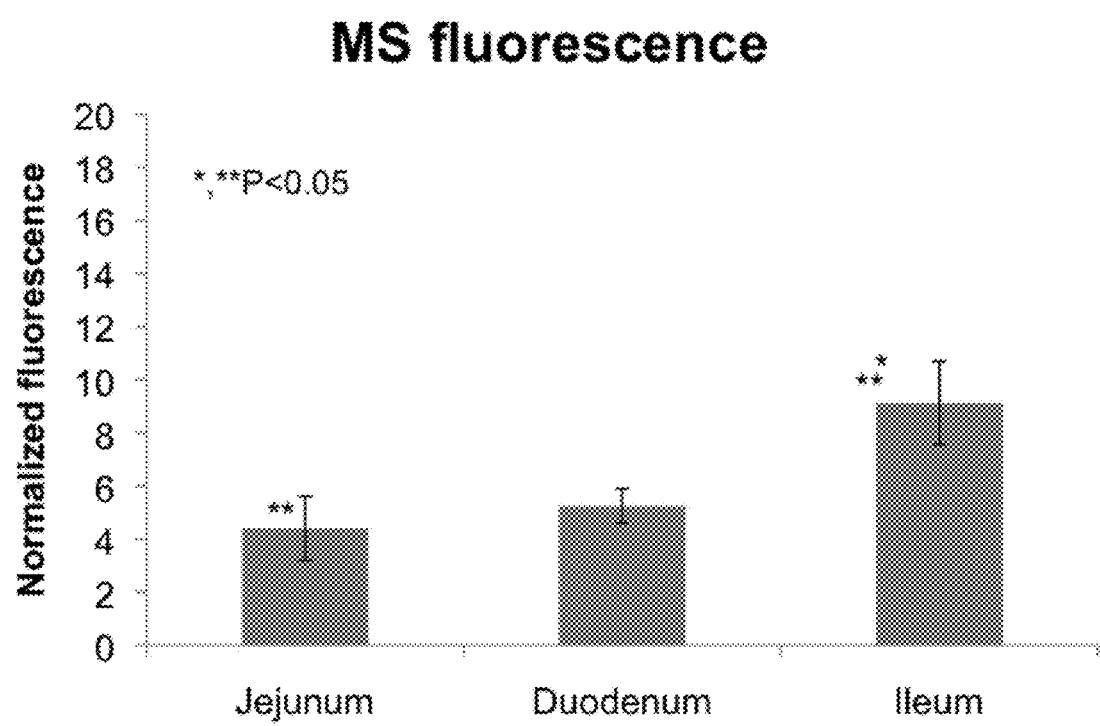
FIG. 1 depicts the normalized fluorescence and images of aldehyde-coated fluorescent microspheres (f-MS) on the surfaces of tissues from three regions of the small intestine.

Improved compositions and methods have been developed for adhering, sealing, or treating one or more biological tissues. Generally, these adhesive formulations comprise a dendrimer component and a polymer component. In some embodiments, the adhesive formulations are used as tissue adhesives, tissue sealants, tissue treatments, matrix materials, fillers, coatings, or a combination thereof.

The adhesive formulations described herein achieve better adhesion, sealing, and/or treatment that previously known adhesives because the dendrimer component has amines on less than 75% of its surface groups.

As used herein, the term "adhering" generally refers to affixing, permanently or temporarily, two or more biological tissues, or two or more regions of a biological tissue. As used herein, the term "sealing" generally refers to covering, at least partially, or filling, at least partially, one or more sites on one or more biological tissues, such as a wound. As used herein, the term "treating" generally refers to improving the response of at least one biological tissue to which one or more adhesive formulations is applied. In some embodiments, the "response" that is improved or enhanced includes inflammation, healing, or both.

Generally, the adhesive formulations may be used on any internal or external biological tissues. The biological tissues may be human or other mammalian tissue. The biological tissues may be natural or artificially generated. The biological tissues may be skin, bone, ocular, muscular, vascular, or an internal organ, such as lung, intestine, heart, liver, etc.

The adhesive formulation can be applied to a tissue site in a human or other animal patient, for example, during a surgical or other medical procedure. In one embodiment, the adhesive formulation is used to create an anastomosis. In some embodiment, the adhesive formulation is used to adhere, seal, and/or treat a wound, lesion, or a combination thereof. For example, the adhesive formulation may be applied to slow-healing or troublesome wounds, such as those suffered by diabetics.

In one embodiment, the adhesive formulation may be used to secure or help secure a medical implant, such as an orthopedic implant, within a human or other animal patient.

Dendrimer Component

In one embodiment, the dendrimer component comprises a dendrimer having amines on less than 75% of its surface groups, which are commonly referred to as "terminal groups" or "end groups." As used herein, the term "dendrimer" refers to any compound with a polyvalent core covalently bonded to two or more dendritic branches. In one embodiment, the amines are primary amines. In another embodiment, the amines are secondary amines. In yet another embodiment, one or more surface groups have at least one primary and at least one secondary amine.

In one embodiment, the dendrimer extends through at least 2 generations. In another embodiment, the dendrimer extends through at least 3 generations. In yet another embodiment, the dendrimer extends through at least 4 generations. In still another embodiment, the dendrimer extends through at least 5 generations. In a further embodiment, the dendrimer extends through at least 6 generations. In still a further embodiment, the dendrimer extends through at least 7 generations.

In one embodiment, the dendrimer may have a molecular weight from about 1,000 to about 1,000,000 Daltons. In a further embodiment, the dendrimer may have a molecular weight from about 3,000 to about 120,000 Daltons. In another embodiment, the dendrimer may have a molecular weight from about 10,000 to about 100,000 Daltons. In yet another embodiment, the dendrimer may have a molecular weight from about 20,000 to about 40,000 Daltons.

Generally, the dendrimer may be made using any known methods. In one embodiment, the dendrimer is made by oxidizing a starting dendrimer having surface groups comprising at least one hydroxyl group so that at least a portion of the surface groups comprise at least one amine. In another embodiment, the dendrimer is made by oxidizing a starting generation 5 (G5) dendrimer having surface groups comprising at least one hydroxyl group so that at least a portion of the surface groups comprise at least one amine. In yet another embodiment, the dendrimer is made by oxidizing a starting G5 dendrimer having surface groups comprising at least one hydroxyl group so that about 25% of the surface groups comprise at least one amine. In a particular embodiment, the dendrimer is a G5 dendrimer having primary amines on about 25% of the dedrimer's surface groups.

In one embodiment, the dendrimer is a poly(amidoamine)-derived (PAMAM) dendrimer. In another embodiment, the dendrimer is a G5 PAMAM-derived dendrimer. In yet another embodiment, the dendrimer is a G5 PAMAM-derived dendrimer having primary amines on about 25% of the dendrimer's surface groups.

In one embodiment, the dendrimer is a poly(propyleneimine)-derived dendrimer.

In certain embodiments, the dendrimer component is combined with a liquid to form a dendrimer component solution. In one embodiment, the dendrimer component solution is an aqueous solution. In one embodiment, the solution comprises water, phosphate buffer saline (PBS), Dulbecco's Modified Eagle's Medium (DMEM), or any combination thereof. In one embodiment, the dendrimer component concentration in the dendrimer component solution is about 5% to about 25% by weight. In another embodiment, the dendrimer component concentration in the dendrimer component solution is about 10% to about 20% by weight. In a further embodiment, the dendrimer component concentration in the dendrimer component solution is about 11% to about 15% by weight.

In some instances, the dendrimer component or dendrimer component solution may further comprise an additive. Generally, the amount of additive may vary depending on the application, tissue type, concentration of the dendrimer component solution, the type of dendrimer component, concentration of the polymer component solutions, and/or the type of polymer component. Example of suitable additives, include but are not limited to, pH modifiers, thickeners, antimicrobial agents, colorants, surfactants, and radio-opaque compounds. Specific examples of these types of additives are described herein. In one embodiment, the dendrimer component solution comprises a foaming additive.

In particular embodiments, the dendrimer component or dendrimer component solution comprises at least one drug. In such embodiments, the adhesive formulation may serve as a matrix material for controlled release of drug. The drug may be essentially any drug suitable for local, regional, or systemic administration from a quantity of the adhesive formulation that has been applied to one or more tissue sites in a patient. In one embodiment, the drug comprises a thrombogenic agent. Non-limiting examples of thrombogenic agents include thrombin, fibrinogen, homocysteine, estramustine, and combinations thereof. In another embodiment, the drug comprises an anti-inflammatory agent. Non-limiting examples of anti-inflammatory agents include indomethacin, salicyclic acid acetate, ibuprophen, sulindac, piroxicam, naproxen, and combinations thereof. In still another embodiment, the drug comprises an anti-neoplastic agent. In still other embodiments, the drug is one for gene therapy. For example, the drug may comprise siRNA molecules to combat cancer. Other drugs are envisioned.

In other particular embodiments, the dendrimer component or dendrimer component solution comprises one or more cells. For example, the adhesive formulation may serve as a matrix material for delivering cells to a tissue site at which the adhesive formulation has been applied. In embodiments, the cells may comprise endothelial cells (EC), endothelial progenitor cells (EPC), hematopoietic stem cells, or other stem cells. In one embodiment, the cells are capable of releasing factors to treat cardiovascular disease and/or to reduce restenosis. Other types of cells are envisioned.

Polymer Component

Generally, the polymer component comprises a polymer with one or more functional groups capable of reacting with one or more functional groups on a biological tissue and/or one or more functional groups on the dendrimer component.

In certain embodiments, the polymer is at least one polysaccharide. In these embodiments, the at least one polysaccharide may be linear, branched, or have both linear and branched sections within its structure. Generally, the at least one polysaccharide may be natural, synthetic, or modified—for example, by cross-linking, altering the polysaccharide's substituents, or both. In one embodiment, the at least one polysaccharide is plant-based. In another embodiment, the at least one polysaccharide is animal-based. In yet another embodiment, the at least one polysaccharide is a combination of plant-based and animal-based polysaccharides. Non-limiting examples of polysaccharides include, but are not limited to, dextran, chitin, starch, agar, cellulose, hyaluronic acid, or a combination thereof.

In certain embodiments, the at least one polymer has a molecular weight from about 1,000 to about 1,000,000 Daltons. In one embodiment, the at least one polymer has a molecular weight from about 5,000 to about 15,000 Daltons. Unless specified otherwise, the "molecular weight" of the polymer refers to the number average molecular weight.

In some embodiments, the polymer is functionalized so that its structure includes one or more functional groups that will react with one or more functional groups on a biological tissue and/or one or more functional groups on the dendrimer component. In one embodiment, the one or more functional groups incorporated into the polymer's structure is aldehyde.

In certain embodiments, the polymer's degree of functionalization is adjustable. The "degree of functionalization" generally refers to the number or percentage of reactive groups on the polymer that are replaced or converted to the desired one or more functional groups. In one embodiment, the degree of functionalization is adjusted based on the type of tissue to which the adhesive is applied, the concentration(s) of the components, and/or the type of polymer or dendrimer used in the adhesive. In one embodiment, the degree of functionalization is from about 10% to about 75%. In another embodiment, the degree of functionalization is from about 15% to about 50%. In yet another embodiment, the degree of functionalization is from about 20% to about 30%.

In one embodiment, the polymer is dextran with a molecular weight of about 10 kDa. In another embodiment, the polymer is dextran having about 50% of its hydroxyl group converted to aldehydes. In a further embodiment, the polymer is dextran with a molecular weight of about 10 kDa and about 50% of its hydroxyl groups converted to aldehydes.

In some embodiments, a polysaccharide is oxidized to include a desired percentage of one or more aldehyde functional groups. Generally, this oxidation may be conducted using any known means. For example, suitable oxidizing agents include, but are not limited to, periodates, hypochlorites, ozone, peroxides, hydroperoxides, persulfates, and percarbonates. In one embodiment, the oxidation is performed using sodium periodate. Typically, different amounts of oxidizing agents may be used to alter the degree of functionalization.

In certain embodiments, the polymer component is combined with a liquid to form a polymer component solution. In one embodiment, the polymer component solution is an aqueous solution. In one embodiment, the solution comprises water, PBS, DMEM, or any combination thereof.

Generally, the polymer component solution may have any suitable concentration of polymer component. In one embodiment, the polymer component concentration in the polymer component solution is about 5% to about 40% by weight. In another embodiment, the polymer component concentration in the polymer component solution is about 5% to about 30% by weight. In yet another embodiment, the polymer component concentration in the polymer component solution is about 5% to about 25% by weight. Typically, the concentration may be tailored and/or adjusted based on the particular application, tissue type, and/or the type and concentration of dendrimer component used.

The polymer component or polymer component solution may also comprise one or more additives. In one embodiment, the additive is compatible with the polymer component. In another embodiment, the additive does not contain primary or secondary amines. Generally, the amount of additive varies depending on the application, tissue type, concentration of the polymer component solution, the type of polymer component and/or dendrimer component. Examples of suitable additives, include, but are not limited to, pH modifiers, thickeners, antimicrobial agents, colorants, surfactants, and radio-opaque compounds. In other embodiments, the polymer component solution comprises a foaming agent.

In certain embodiments, the pH modifier is an acidic compound. Examples of acidic pH modifiers include, but are not limited to, carboxylic acids, inorganic acids, and sulfonic acids. In other embodiments, the pH modifier is a basic compound. Examples of basic pH modifiers include, but are not limited to, hydroxides, alkoxides, nitrogen-containing compounds other than primary and secondary amines, basic carbonates, and basic phosphates.

Generally, the thickener may be selected from any known viscosity-modifying compounds, including, but not limited to, polysaccharides and derivatives thereof, such as starch or hydroxyethyl cellulose.

Generally, the surfactant may be any compound that lowers the surface tension of water. In one embodiment, the surfactant is an ionic surfactant—for example, sodium lauryl sulfate. In another embodiment, the surfactant is a neutral surfactant. Examples of neutral surfactants include, but are not limited to, polyoxyethylene ethers, polyoxyethylene esters, and polyoxyethylene sorbitan.

In one embodiment, the radio-opaque compound is barium sulfate, gold particles, or a combination thereof.

In particular embodiments, the polymer component or polymer component solution comprises at least one drug. In such embodiments, the adhesive formulation may serve as a matrix material for controlled release of drug. The drug may be essentially any drug suitable for local, regional, or systemic administration from a quantity of the adhesive formulation that has been applied to one or more tissue sites in a patient. In one embodiment, the drug comprises a thrombogenic agent. Non-limiting examples of thrombogenic agents include thrombin, fibrinogen, homocysteine, estramustine, and combinations thereof. In another embodiment, the drug comprises an anti-inflammatory agent. Non-limiting examples of anti-inflammatory agents include indomethacin, salicyclic acid acetate, ibuprophen, sulindac, piroxicam, naproxen, and combinations thereof. In still another embodiment, the drug comprises an anti-neoplastic agent. In still other embodiments, the drug is one for gene or cell therapy. For example, the drug may comprise siRNA molecules to combat cancer. Other drugs are envisioned.

In other particular embodiments, the polymer component or polymer component solution comprises one or more cells. For example, the adhesive formulation may serve as a matrix material for delivering cells to a tissue site at which the adhesive formulation has been applied. In embodiments, the cells may comprise endothelial cells (EC), endothelial progenitor cells (EPC), hematopoietic stem cells, or other stem cells. In one embodiment, the cells are capable of releasing factors to treat cardiovascular disease and/or to reduce restenosis. Other types of cells are envisioned.

Adhesive Formulation

Generally, the adhesive formulations described herein may be formed by combining the polymer component or polymer component solution, and the dendrimer component or dendrimer component solution in any manner. In some embodiments, the polymer component or polymer component solution, and the dendrimer component or dendrimer component solution are combined before contacting a biological tissue with the adhesive formulation. In other embodiments, the polymer component or polymer component solution, and the dendrimer component or dendrimer component solution are combined, in any order, on a biological tissue. In further embodiments, the polymer component or polymer component solution is applied to a first biological tissue, the dendrimer component or dendrimer component solution is applied to a second biological tissue, and the first and second biological tissues are contacted. In still a further embodiment, the polymer component or polymer component solution is applied to a first region a biological tissue, the dendrimer component or dendrimer component solution is applied to a second region of a biological tissue, and the first and second regions are contacted.

Generally, the adhesive formulation may be applied to one or more biological tissues as an adhesive, sealant, and/or treatment. The one or more biological tissues may be diseased or healthy. In one embodiment, the adhesive formulation is applied to one or more biological tissues as an adhesive. In another embodiment, the adhesive formulation is applied to one or more biological tissues as a sealant. In a further embodiment, the adhesive formulation is applied to one or more biological tissues as a treatment. In an additional embodiment, the adhesive formulation is applied to one or more biological tissues as an adhesive and sealant. In still another embodiment, the adhesive formulation is applied to one or more biological tissues as an adhesive and treatment. In yet another embodiment, the adhesive formulation is applied to one or more biological tissues as a sealant and treatment. In a still further embodiment, the adhesive formulation is applied to one or more biological tissues as an adhesive, sealant, and treatment.

As used herein, the adhesive formulation is a "treatment" when it improves the response of at least one biological tissue to which it is applied. In some embodiments, the improved response is lessening overall inflammation, improving the specific response at the wound site/interface of the tissue and adhesive formulation, enhancing healing, or a combination thereof. As used herein, the phrase "lessening overall inflammation" refers to an improvement of histology scores that reflect the severity of inflammation. As used herein, the phrase "improving the specific response at the wound site/interface of the tissue and adhesive formulation" refers to an improvement of histology scores that reflect the severity of serosal neutrophils. As used herein, the phrase "enhancing healing" refers to an improvement of histology scores that reflect the severity of serosal fibrosis.

After contacting one or more biological tissues, the adhesive formulations may be allowed adequate time to cure or gel. When the adhesive formulation "cures" or "gels," as those terms are used herein, it means that the reactive groups on the polymer component, dendrimer component, and one or more biological tissues have undergone one or more reactions. Not wishing to be bound by any particular theory, it is believed that the adhesive formulations described herein are effective because the polymer component reacts with both the dendrimer component and the surface of the biological tissues. In certain embodiments, the polymer component's aldehyde functional groups react with the amines on the dendrimer component and the biological tissues to form imine bonds. In these embodiments, it is believed that the amines on the dendrimer component react with a high percentage of the aldehydes on the polymer component, thereby reducing toxicity and increasing biocompatibility of the adhesive formulations. Typically, the time needed to cure or gel the adhesive formulations will vary based on a number of factors, including, but not limited to, the characteristics of the polymer component and/or dendrimer component, the concentrations of the polymer component solution and/or the dendrimer component solution, and the characteristics of the one or more biological tissues. In embodiments, the adhesive formulation will cure sufficiently to provide desired bonding or sealing shortly after the components are combined. The gelation or cure time should provide that a mixture of the components can be delivered in fluid form to a target area before becoming too viscous or solidified and then once applied to the target area sets up rapidly thereafter. In one embodiment, the gelation or cure time is less than 120 seconds. In another embodiment, the gelation or cure time is between 3 and 60 seconds. In a particular embodiment, the gelation or cure time is between 5 and 30 seconds.

In certain embodiments, one or more foaming agents are added to the polymer component solution and/or the dendrimer component solution before the solutions are combined. In one embodiment, the foaming agents comprise a two part liquid system comprising Part 1 and Part 2, wherein Part 1 comprises a bicarbonate and Part 2 comprises an aqueous solution of di- or polyaldehydes and a titrant. A wide range of di- or polyaldhydes exist, and their usefulness is restricted largely by availability and by their solubility in water. For example, aqueous glyoxal (ethanedial) is useful, as is aqueous glutaraldehyde (pentadial). Water soluble mixtures of di- and polyaldehydes prepared by oxidative cleavage of appropriate carbohydrates with periodate, ozone or the like may also be useful.

A titrant is most preferably employed in the liquid solution of Part 2. More specifically, the titrant is an organic or inorganic acid, buffer, salt, or salt solution which is capable of reacting with the bicarbonate component of Part 1 to generate carbon dioxide and water as reaction by-products. The carbon dioxide gas that is generated creates a foam-like structure of the adhesive formulation and also causes the volume of the adhesive formulation to expand.

Most preferably, the titrant is an inorganic or organic acid that is present in an amount to impart an acidic pH to the resulting mixture of the Part 1 and Part 2 components. Preferred acids that may be employed in the practice of the present invention include phosphoric acid, sulfuric acid, hydrochloric acid, acetic acid, and citric acid.

Tissue Specific Formulations

Generally, the polymer component and the dendrimer component that are combined to form the adhesive formulation may be tailored for specific biological tissues. For example, the type of components or the amounts of one or both of the components may be adjusted. Not wishing to be bound by any particular theory, it is believed that performing an analysis to determine the density of amine groups on the surface of a biological tissue may guide the determination of how to alter the adhesive formulations. In one embodiment, aldehyde-coated fluorescent microspheres (f-MS) are applied to various tissues to aid this analysis.

Generally, the adhesive formulations may be adjusted in any manner to compensate for differences between tissues. In one embodiment, the amount of polymer component is increased or decreased while the amount of dendrimer component is unchanged. In another embodiment, the amount of dendrimer component is increased or decreased while the amount of polymer component is unchanged. In another embodiment, the concentration of the polymer component solution is increased or decreased while the dendrimer component or dendrimer component solution is unchanged. In yet another embodiment, the concentration of the dendrimer component solution is increased or decreased while the polymer component or polymer component solution is unchanged. In a further embodiment, the concentrations of the both the polymer component solution and the dendrimer component solution are changed.

When the amine density on the surface of a particular biological tissue is unknown due to disease, injury, or otherwise, an excess of polymer component or polymer component solution may, in some embodiments, be added when the adhesive formulation is first applied, then the amount of polymer component or polymer component solution may be reduced, e.g., incrementally or drastically, until the desired effect is achieved. The "desired effect," in this embodiment, may be an appropriate or adequate curing time, adhesion, sealing, or a combination thereof. Not wishing to be bound by any particular theory, it is believed that an excess of polymer component or polymer component solution may be required, in some instances, to obtain the desired effect when the amine density on a biological tissue is low. Therefore, adding an excess will help the user, in this embodiment, achieve adequate sealing or adhesion in less time. This is particularly desirable in emergency situations.

In other embodiments, however, a lower amount of polymer component or polymer component solution may be added when the adhesive formulation is first applied, then the amount of polymer component or polymer component solution may be increased, e.g., incrementally or drastically, until the desired effect is achieved, which may be adequate curing time, adhesion, sealing, or a combination thereof.

Adhesive Formulation Kits

In another aspect, a kit is provided that comprises a first part that includes a polymer component or polymer component solution, and a second part that includes a dendrimer component or dendrimer component solution. The kit may further include an applicator or other device means, such as a multi-compartment syringe, for storing, combining, and delivering the two parts and/or the resulting adhesive formulation to a tissue site.

In one embodiment, the kit comprises separate reservoirs for the polymer component solution and the dendrimer component solution. In certain embodiments, the kit comprises reservoirs for polymer component solutions of different concentrations. In other embodiments, the kit comprises reservoirs for dendrimer component solutions of different concentrations.

In one embodiment, the kit comprises instructions for selecting an appropriate concentration or amount of at least one of the polymer component, polymer component solution, dendrimer component, or dendrimer component solution to compensate or account for at least one characteristic of one or more biological tissues. In one embodiment, the adhesive formulation is selected based on one or more predetermined tissue characteristics. For example, previous tests, such as those described herein, may be performed to determine the number of density of bonding groups on a biological tissue in both healthy and diseased states. Alternatively, a rapid tissue test may be performed to assess the number or density of bonding groups. Quantification of tissue bonding groups can be performed by contacting a tissue with one or more materials that (1) have at least one functional group that specifically interacts with the bonding groups, and (2) can be assessed by way of fluorescence or detachment force required to separate the bonding groups and the material. In another embodiment, when the density of bonding groups on a biological tissue is unknown, an excess of the polymer component, such as one containing aldehydes, may be initially added as described herein to gauge the density of bonding groups on the surface of the biological tissue.

In certain embodiments, the kit comprises at least one syringe. In one embodiment, the syringe comprises separate reservoirs for the polymer component solution and the dendrimer component solution. The syringe may also comprise a mixing tip that combines the two solutions as the plunger is depressed. The mixing tip may be releasably securable to the syringe (to enable exchange of mixing tips), and the mixing tip may comprise a static mixer. In some embodiments, the reservoirs in the syringe may have different sizes or accommodate different volumes of solution. In other embodiments, the reservoirs in the syringe may be the same size or accommodate the same volumes of the solution. In a further embodiment, one reservoir may comprise Part 1 of the foaming composition described hereinabove, and a second reservoir may comprise Part 2 of the foaming composition.

Figure 22:
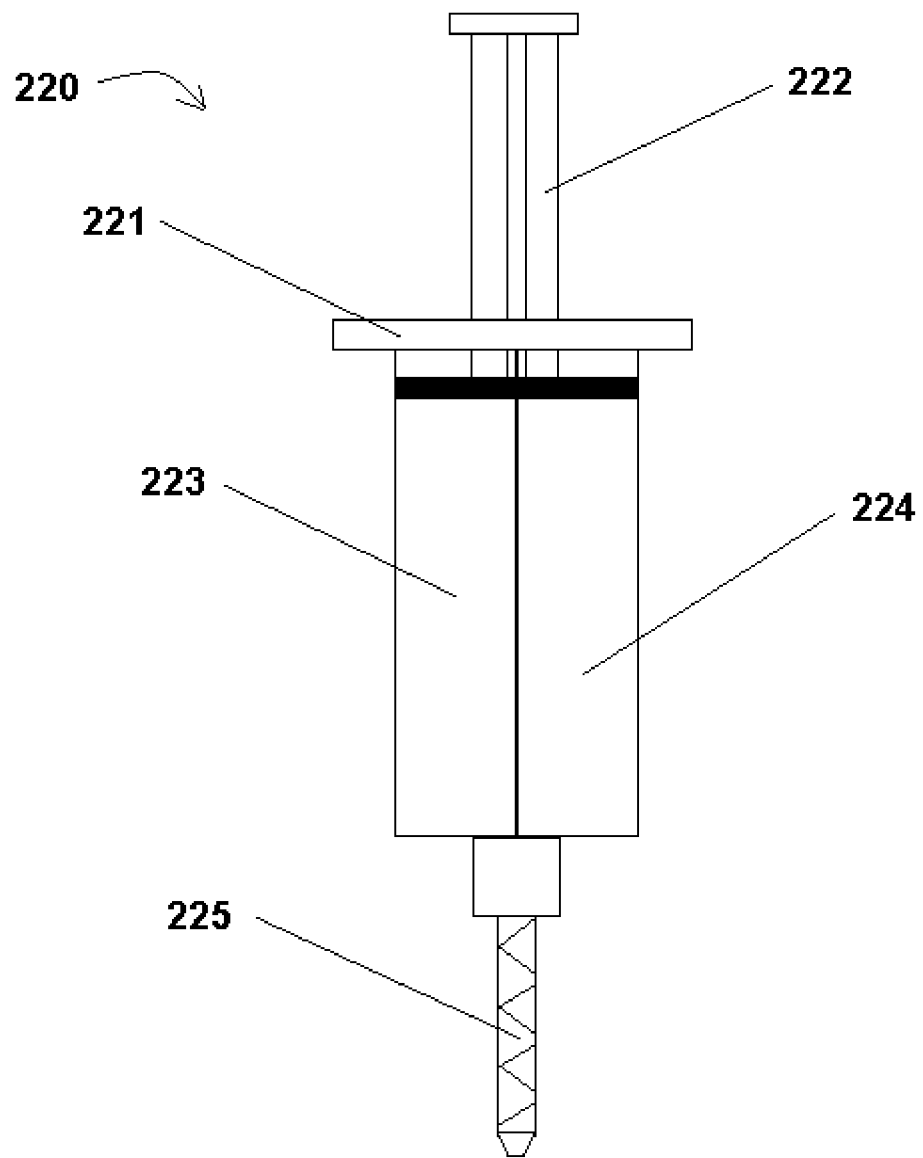
FIG. 22 depicts one embodiment of a kit containing the components of an adhesive formulation.

FIG. 22 depicts one embodiment of a syringe 220. The syringe 220 includes a body 221 with two reservoirs (223, 224). A dendrimer component solution is disposed in the first reservoir 223, and a polymer component solution is disposed in the second reservoir 224. The two reservoirs (223, 224) are emptied by depressing the plunger 222, which pushes the contents of the two reservoirs (223, 224) into the mixing tip 225 and out of the syringe 220.

In a further embodiment, one or more of the reservoirs of the syringe may be removable. In this embodiment, the removable reservoir may be replaced with a reservoir containing a polymer component solution or a dendrimer component solution of a desired concentration.

In a preferred embodiment, the kit is sterile. For example, the components of the kit may be packaged together, for example in a tray, pouch, and/or box. The packaged kit may be sterilized using known techniques such as electron beam irradiation, gamma irradiation, ethylene oxide sterilization, or other suitable techniques.

EXAMPLES

The present invention is further illustrated by the following examples, which are not to be construed in any way as imposing limitations upon the scope thereof. On the contrary, it is to be clearly understood that resort may be had to various other aspects, embodiments, modifications, and equivalents thereof which, after reading the description herein, may suggest themselves to one of ordinary skill in the art without departing from the spirit of the present invention or the scope of the appended claims. Thus, other aspects of this invention will be apparent to those skilled in the art from consideration of the specification and practice of the invention disclosed herein.

Example 1

Preliminary Testing of Various Tissues

The conjugation of aldehyde-coated fluorescent microspheres (f-MS) was used to probe tissue-surface chemistry, and provide a mechanistic basis for the variability in adhesive mechanics. This technique is described in Artzi, N., et al. ADV. MATER. 21, 2009, 1-5.

The technique is used because tissue-tissue interfacial stress is regulated in nature with variations in surface chemistry. Examining these changes helped explain tissue-adhesive formulation interactions, and assisted the development tissue-specific adhesive formulations.

In this example, tissues from three regions of the small intestine were tested: jejunum, duodenum, and ileum. These tissues were selected because chemical differences drive gastrointestinal (GI) tract physiology. The spectrum of contractility and persitalsis, pH, and surface chemistry across the GI bed allow for a profound modulation of nutrition, inflammation, infection, etc. Biopsies of each tissue were prepared with equal surface area (20 mm$^2$) and submerged in 0.5 mL of 0.5% f-MS solutions for 20 minutes on a rocker at 37° C. The tissue samples then were thoroughly rinsed with 10 mL PBS three times. Following rinsing, the fluorescent intensity at the surface of the tissue samples was measured. Images were obtained with a fluorescence microscope to confirm the presence of the f-MS. A fluoroscein isothiocyanate (FITC) filter was used for fluorescein and tetramethylrhodamine isothiocyanate (TRITC) for propidium iodide (tissue staining).

The normalized fluorescence of the f-MS on the surface of each tissue sample is shown in FIG. 1. The tissues from the three regions of the small intestine had surfaces with different numbers of amine groups, as demonstrated by the variable fluorescent intensity of the conjugated f-MS. In this figure, a p-value <0.05 was considered to denote statistical significance.

Example 2

Interfacial Fluorescence of a Biocompatible Adhesive

The information concerning natural GI surface chemistry in Example 1 was used to create adhesive formulations that interacted differentially with specific tissues to create adhesive formulations that are more effective GI wall sealants. Leakage of gut content is a frequent surgical complication that can result in local infection and systemic sepsis, peritonitis, and often the need for reoperation. Adhesive formulations were created by matching adhesive formulation and tissue properties. This example determined that differences in tissue surfaces—in this case, amine density in duodenum, jejunum, and ileum—affect interactions with adhesive formulations of varied aldehyde content and densities.

To characterize the adhesive formulation's morphology at the tissue-adhesive interface, the dendrimer component was labeled with fluorescein. This technique is described in Artzi, N., et al. ADV. MATER. 21, 2009, 1-5. The dendrimer used in this example was a G5 dendrimer with 25% of its surface groups having primary amines instead of hydroxyl groups. The dendrimer had a molecular weight of about 30 kDaltons.

The dendrimer was dissolved in 6 mL dimethylsulfoxide, followed by the addition of 0.030 g of 6-(fluorescein-5-carboxyamido)hexanoic acid (Invitrogen, Carlsbad, Calif. 92008) and 12 μL triethylamine. The mixture was stirred at room temperature for 48 h. The resulting solid after solvent evaporation was dissolved in 100 mL water, dialyzed, and lyophilized. The fluorescein-labeled dendrimer was then added to water to create a solution having 1% of the total solid content (12.5%) by weight of the fluorescein-labeled dendrimer (G5-25-12.5)

A separate aqueous solution of dextran was created. The dextran, in this example, had a molecular weight of about 10 kDalton, and 50% of its hydroxyl groups had been converted to aldehydes. The aqueous solution contained 11.25% by weight of the dextran (D10-50-11.25).

The two solutions G5-25-12.5 and D10-50-11.25 were then combined and applied to separate samples of three tissues from different regions of the small intestine: jejunum, duodenum, and ileum. The combination of solutions was allowed to cure for 5 min.

Figure 2:
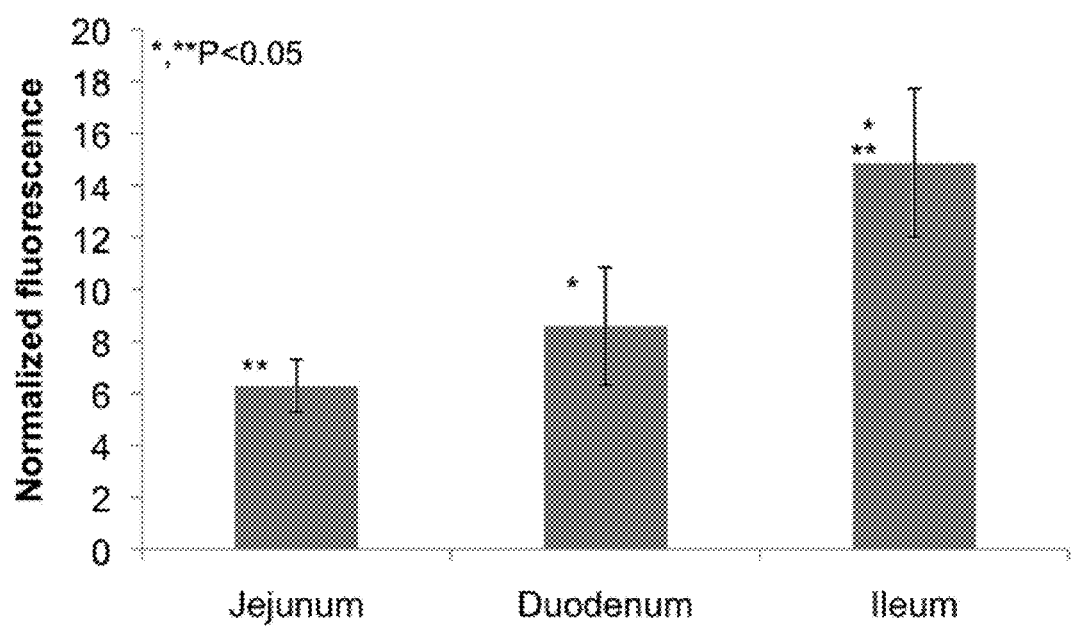
FIG. 2 depicts the interfacial fluorescence and images of a labeled dendrimer:dextran formulation applied to the surfaces of tissues from three regions of the small intestine.

The tissue samples were then cryosectioned (20 μm sections) and stained with propidium iodide. The adhesive's morphology at the tissue:adhesive interface was quantified using image analysis techniques (Leica Microsystems, MetaMorph®) to characterize the transitory material between tissue surface and material bulk. FIG. 2 depicts the interfacial fluorescence of the labeled dendrimer. The differences in normalized fluorescence demonstrated that the labeled dendrimer:dextran (formulation G5-25-12.5:D10-50-11.25) had different reactivity with the three tissue surfaces due to the different amine densities presented by these tissues. In this figure, a p-value <0.05 was considered to denote statistical significance.

Figure 3:
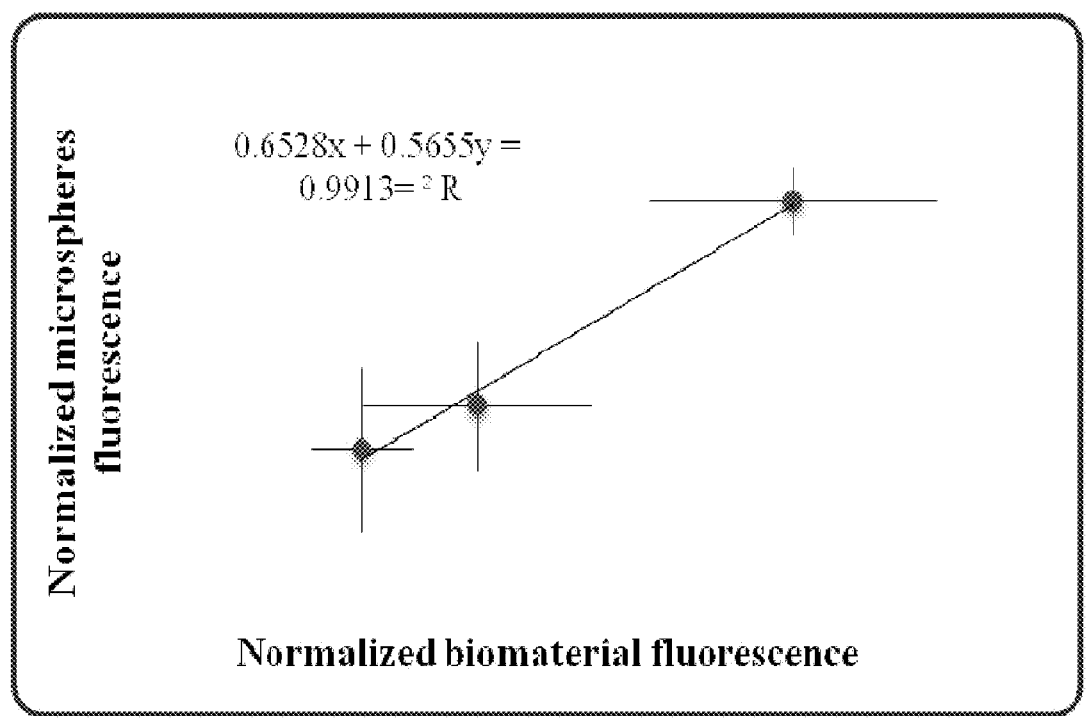
FIG. 3 depicts the correlation between the normalized fluorescence of f-MS and labeled dendrimer:dextran formulations when applied to the surfaces of tissues from three regions of the small intestine.

To demonstrate that the f-MS analysis accurately predicts the interaction of a particular tissue with the labeled dendrimer:dextran (formulation G5-25-12.5:D10-50-11.25), the normalized fluorescence of the f-MS and the normalized fluorescence of the labeled dendrimer were plotted and compared as shown in FIG. 3. In this figure, a linear correlation exists between the normalized fluorescence of the labeled dendrimer (X-axis) and the f-MS. As a result, the f-MS was used as a tool to accurately gauge the behavior of various adhesive compositions when applied to different types of tissue. The information obtained from the f-MS can be used to determine how the dendrimer component, polymer component, and/or solution concentrations should be adjusted to compensate for the varying characteristics of different tissue types. These data supported the notion that the functional groups on tissues and in the adhesive formulations influence aldehyde-mediated adhesive interactions, providing a functional basis for tissue-specific adhesive design. In this example, the microspheres assay correlated with mechanical quantification of adhesion strength measured in the tensile strength tests described herein.

Example 3

Effect of Polymer Component Solution Concentration on Adhesion Strength

The adhesion strength following the application of a biocompatible adhesive to various tissues was measured with monotonic uniaxial tensile testing (Bose® Biodynamic Test Instrument, Minnetonka, Minn., USA). In this example, three adhesive formulations were applied to three tissues from the small intestine. The three adhesive formulations contained the same dendrimer component solution: the G5-25-12.5 solution described in Example 2. Each polymer component solution contained various concentrations of a dextran (D10-50) with a molecular weight of 10 kDaltons, and 50% of its hydroxyl groups converted to aldehydes. The first polymer component solution had a dextran concentration of 25% by weight (D10-50-25), the second polymer component solution had a dextran concentration of 15% by weight (D10-50-15), and the third polymer component solution had a dextran concentration of 11.25% by weight (D10-50-11.25).

Each individual dextran solution was combined with an equal volume of the dendrimer solution to create three formulations: (1) D10-50-25:G5-25-12.5, (2) D10-50-15: G5-25-12.5, and (3) D10-50-11.25:G5-25-12.5. Adhesive test elements were created by evenly distributing 200 µL of these adhesive formulations between two uniformly sized tissue biopsies (discs of 8 mm diameter, total test element thickness of 1 mm). All three formulations were tested on three tissues from various regions of the small intestine: ileum, jejunum, and duodenum. The tissue surfaces were gently dried prior to applying the adhesive formulation.

Figure 4:
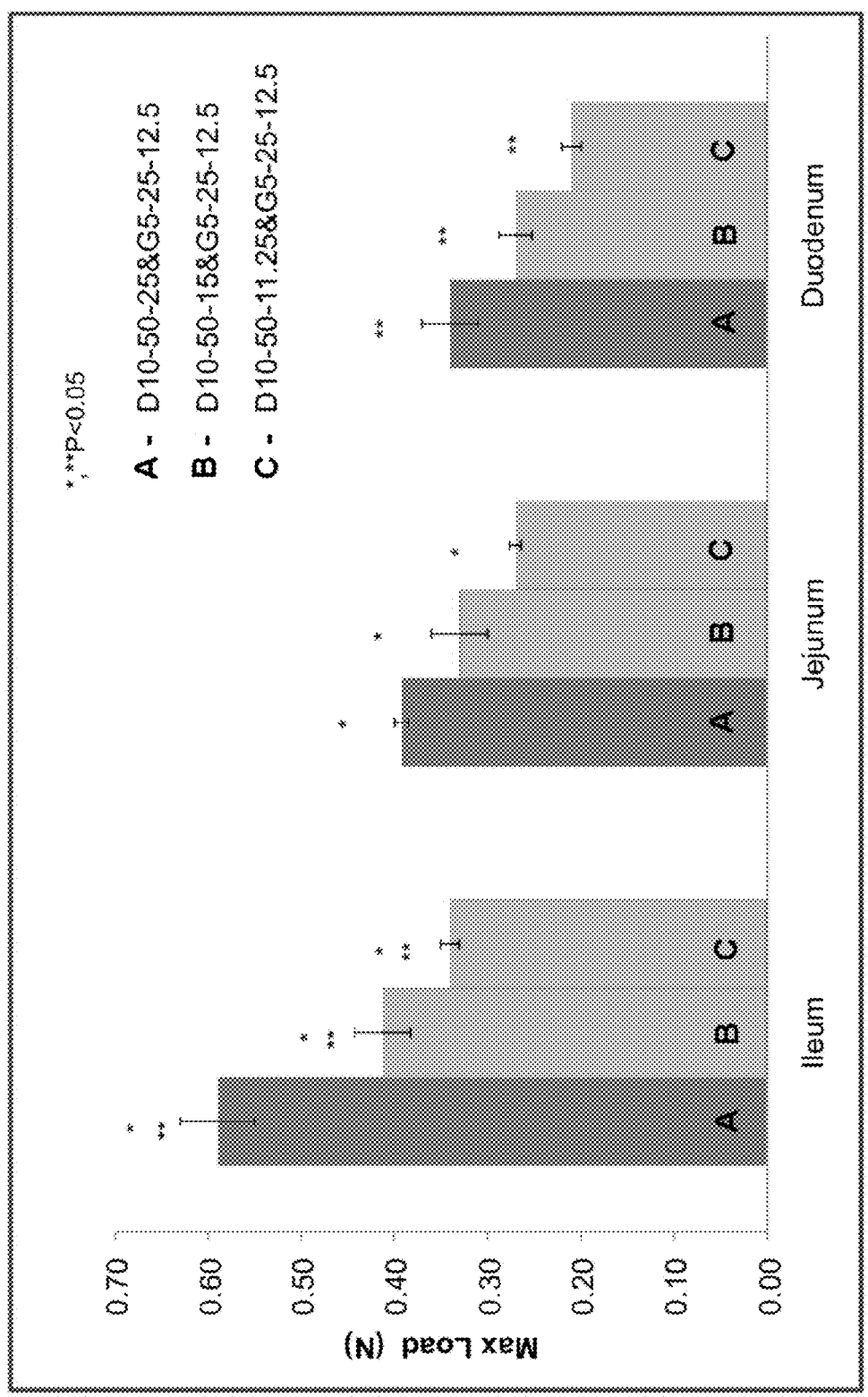
FIG. 4 depicts the maximum load of three adhesive formulations that contain dextran solutions of different concentrations.

After applying each formulation between tissue surfaces and allowing 5 minutes for curing, the adhesive test elements were displaced at a constant rate of 0.05 mm/s, and the load response was continuously recorded (200 measurements/s). Recorded loads were normalized to account for adhesive test element cross-sectional area. The max load (N) of each formulation on each tissue type is shown in FIG. 4. On all three tissues, increasing the concentration of the dextran solution increased the maximum load. Therefore, altering the concentration of the polymer component solution—in this example, a dextran-containing solution—can compensate for the different structures and chemical makeup of various types of tissues. In this figure, a p-value <0.05 was considered to denote statistical significance.

The max load (N) of three additional formulations and their adhesion to the jejunum was also tested. Like the above-described formulations, each contained dendrimer component solutions of the same concentration—in this case, G5-25, 12.5. However, different concentrations of polymer component solutions were used to make each formulation: 7.5% by weight, 9.375% by weight, and 20% by weight. Therefore, the three additional formulations were (4) D10-50-7.5:G5-25-12.5, (5) D10-50-9.375:G5-25-12.5, and (6) D10-50-20:G5-25-12.5.

Figure 5:
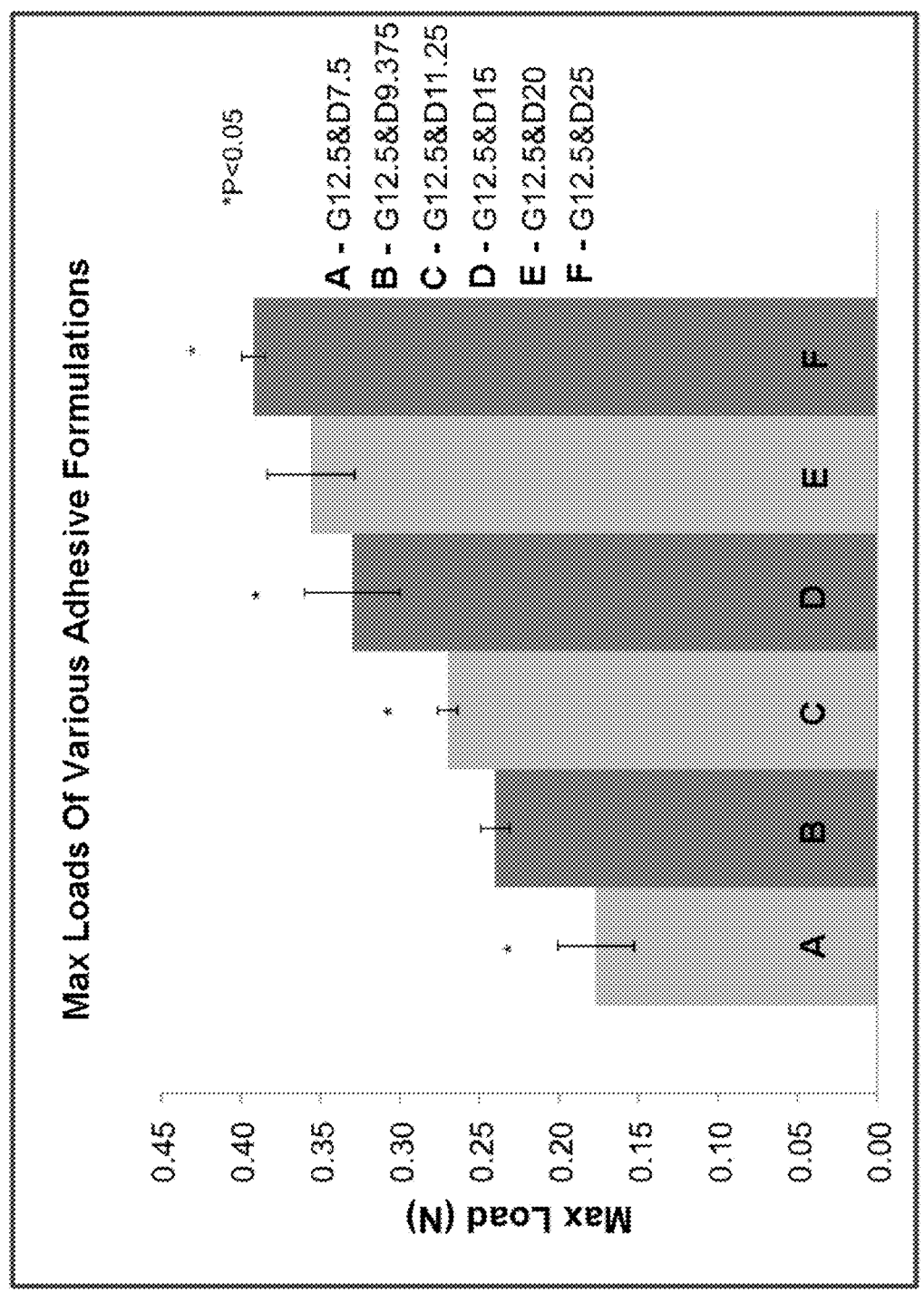
FIG. 5 depicts the maximum load at failure for different adhesive formulations containing dextran solutions of different concentrations.

The max loads (N) of these three additional formulations and the previously-described formulations are shown in FIG. 5. As the concentration of the polymer component solution increased, the max load (N) increased. This result further illustrated how adjusting the concentration of the polymer component solution can be used to compensate for the differences between tissues. In this figure, a p-value <0.05 was considered to denote statistical significance. Images were obtained of the adhesive formulations tested in FIG. 5 after being applied to the jejunum tissues. The images were obtained by tagging 1% of the dendrimer with 6-(fluorescein-5-carboxyamido)hexanoic acid before applying the formulation to the jejunum. The jejunum was then frozen with liquid nitrogen and maintained at −80° C. overnight. The tissue was then cryosectioned (20 µm sections) and stained with propidium iodide. Fluorescence microscopy images were taken using FITC (material, fluorescein) and TRITC (tissue, propidium iodide) filters. The images revealed the interface between the tissues and the adhesive formulations.

Figure 6:
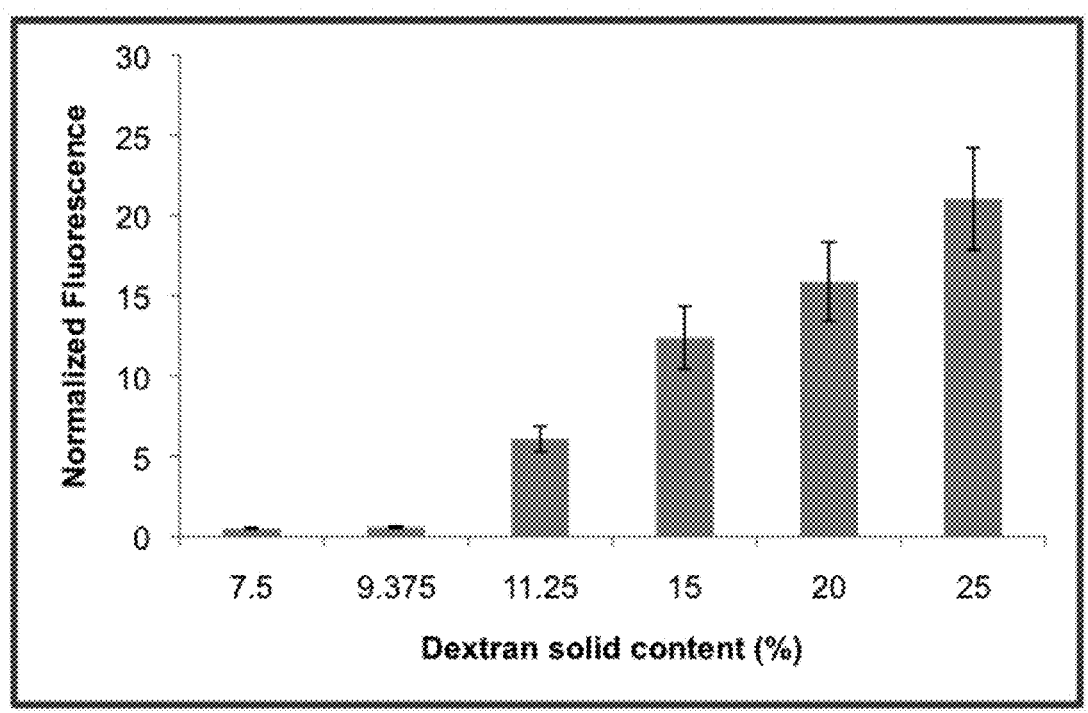
FIG. 6 depicts the fluorescence at the interface between various adhesive formulations and jejunum tissues.
Figure 7:
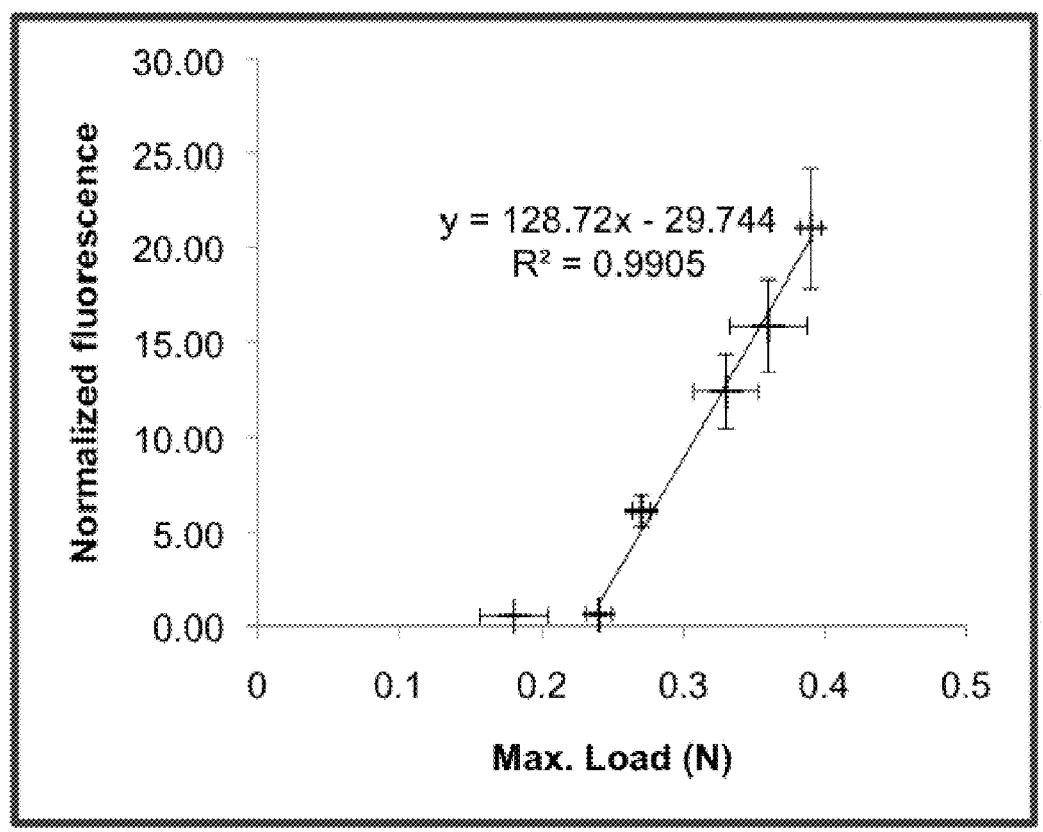
FIG. 7 depicts the correlation between fluorescence (surrogate for tissue amine content) and max load of adhesive formulations applied to the jejunum.

The fluorescence at the interface between the jejunum and the adhesive formulations of FIG. 5 was also measured. As shown in FIG. 6, the normalized fluorescence increased as the concentration of polymer component solution—in this case, a dextran solution—increased. In addition to correlating with the concentration of the polymer component solution, the normalized fluorescence also correlated with the max load of the adhesive formulations applied to the jejunum. This relationship is illustrated in FIG. 7. These relationships showed how the analytical techniques described herein can be used to predict and estimate the changes that should be made to the adhesive formulations to compensate for a number of variables, including the characteristics of different tissue types. These tests also allow for determining how the state of a disease and its severity can alter the number and functionality of chemical groups on tissue surfaces.

Example 4

Biocompatibility of Various Adhesive Formulations

The biocompatibility of three of the adhesive formulations described in Example 3 were tested using 3T3 fibroblasts. The three adhesive formulations were (a) D10-50-7.5:G5-25-12.5, (b) D10-50-15:G5-25-12.5, and (c) D10-50-25:G5-25-12.5. The cell survival was measured after 1 day, 1 week, and 1 month.

Figure 8:
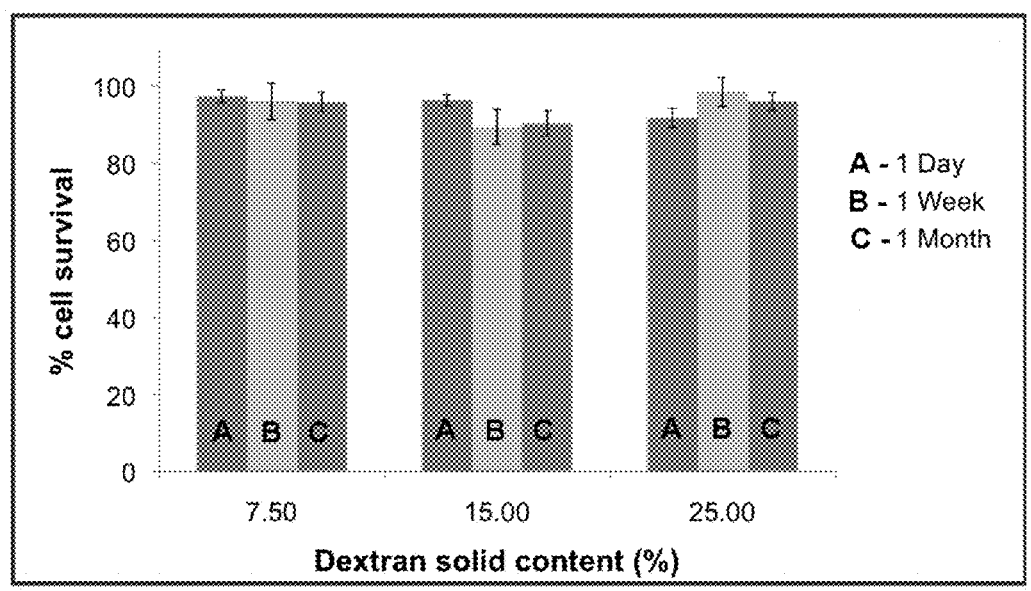
FIG. 8 depicts the biocompatibility of several adhesive formulations using 3T3 fibroblasts.

Adhesive disks of 5 mm diameter were kept in 5 mL of media at 37° C. for 1 day, 1 week, and 1 month. At each interval, 100K 3T3 fibroblasts were incubated for 24 hours in 1 mL of media containing the degradation products of the disks. After 24 hours, cell death was measured using CytotoxONE Membrane Integrity Assay (Promega Corp., Madison, Wis., USA), and the number of dead cells was normalized to the total number of both live and dead cells. The number of live cells was determined by trypsinizing and counting the cells. As shown in FIG. 8, the biocompatibility test showed very high cell survival. Images of the adhesive formulations implanted into the tissue of mice also showed good biocompatibility.

Figure 9:
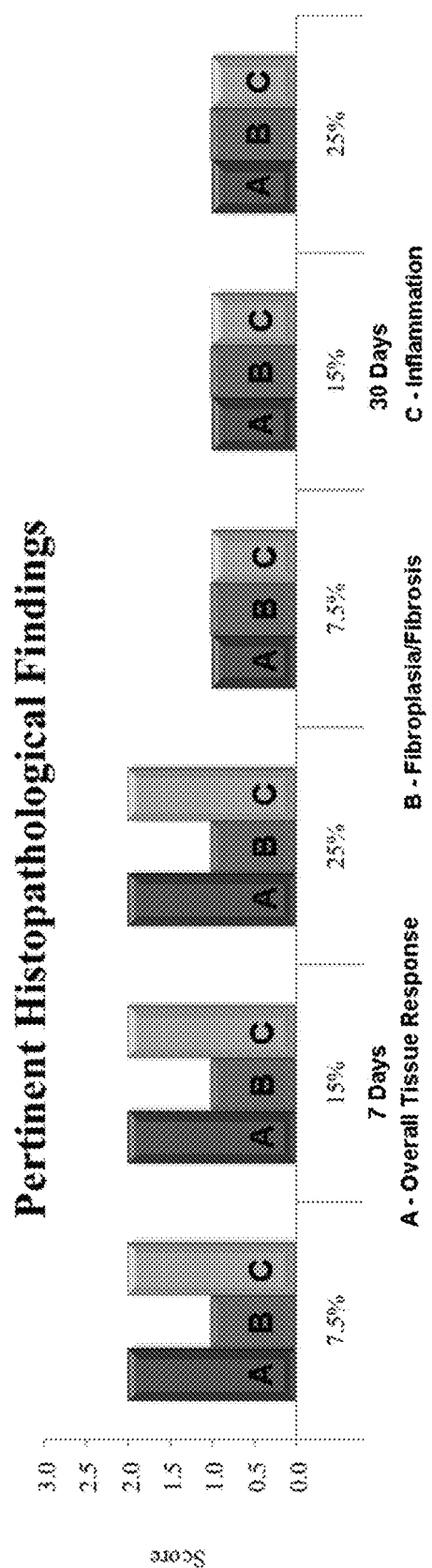
FIGS. 9 and 10 depict pertinent histopathological findings for various adhesive formulations.
Figure 10:
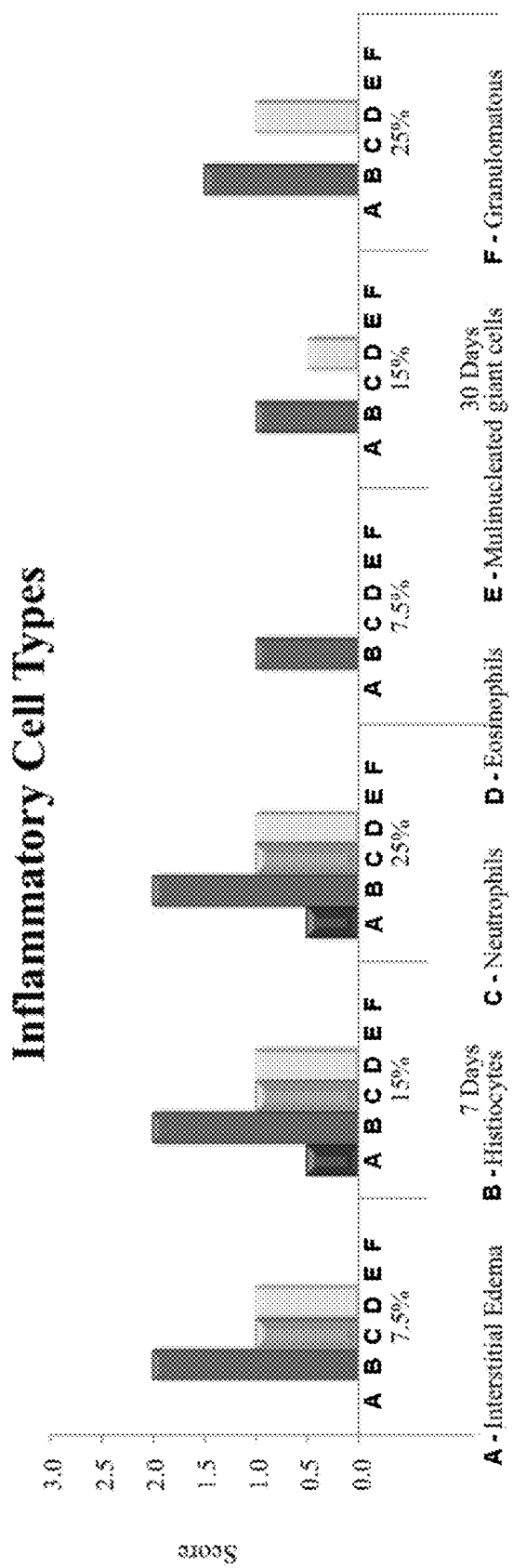

Similarly, FIGS. 9 and 10 depict pertinent histopathological findings of various adhesive formulations. In this test, 15 µm tissue sections were stained with Hematoxylin and Eosin for semi-quantitative scoring (i.e., 1=minimal, 2=mild, 3=severe) of pertinent parameters (e.g., inflammation, fibrosis, giant cells etc.) for each dose group by time point.

Example 5

Comparison of Gelation Times for Various Adhesive Formulations

The gelation times for several adhesive formulations described herein were compared to each other, and to adhesives made using polyethylene glycol (PEG) amine and dextran. The gelation time in this example is the time required for the two components to form an adhesive hydrogel, which is indicative of crosslinking density and stiffness.

Figure 11:
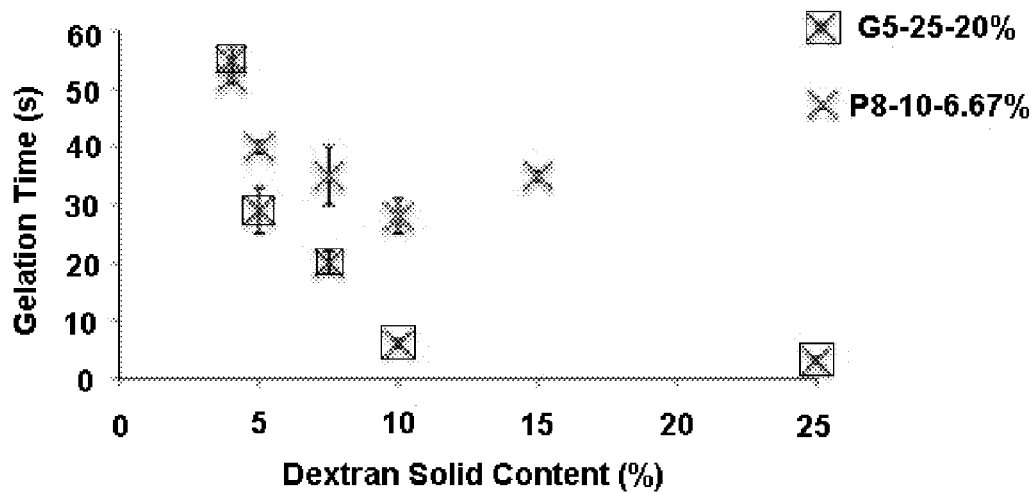
FIG. 11 depicts a comparison of gelation times for adhesive formulations described herein and several adhesives containing aminated poly(ethyleneglycol).

Six different adhesive formulations, as described herein, were produced for this test. Each adhesive formulation consisted of combination of G5-25-20 (which is a 20% by weight aqueous solution of a G5 dendrimer with 25% of its surface groups having primary amines instead of hydroxyl groups) and various concentrations of an aqueous solution of D10-50, which is a 10 kDalton dextran with 50% of its hydroxyl groups replaced with aldehydes. The concentrations, by weight percent, of the D10-50 solutions were 4, 5, 7.5, 10, 15, and 25. As shown in FIG. 11, the gelation times for the adhesive compositions with polymer component solution concentrations of 10, 15, and 25% by weight were very similar, and much shorter than the gelation times for the adhesive compositions with polymer component solution concentrations of 4, 5, and 7.5% by weight.

FIG. 11 also includes the gelation times of various adhesives containing PEG amine and dextran (D10-50). The PEG amine in this example was an eight-armed polyether with primary amines at the end of each arm, and a molecular weight of 10 kDalton. A 6.67% by weight aqueous solution of PEG-amine—referred to in this example as P8-10-6.67—was combined with dextran solutions of the following concentrations: 4, 5, 10, 15, and 25% by weight. The gelation times of these six PEG adhesives are plotted in FIG. 11. For comparison purposes, all of the adhesive formulations compared in FIG. 11 were formulated so that each had the same number of either PEG amine molecules or dendrimer molecules.

As shown in FIG. 11, the gelation times of the dendrimer-containing adhesive formulations were faster than those of the PEG amine adhesives at every concentration of dextran. Not wishing to be bound by any particular theory, this discrepancy may be caused by the lower steric hindrance of the dendrimer component of the adhesive formulations described herein; therefore, the reaction between the dendrimer component and the dextran is more likely to occur than the reaction between PEG amine and dextran.

Figure 12:
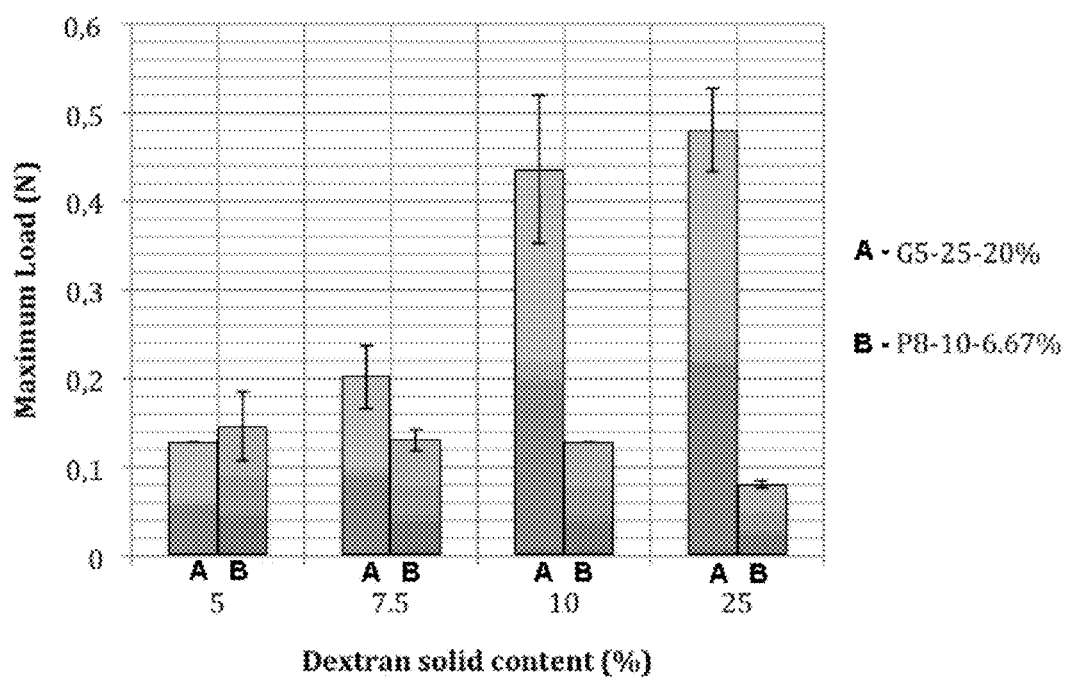
FIG. 12 depicts the maximum load of various adhesive formulations containing dendrimer or PEG amine.

The maximum load of the adhesives of FIG. 11 are plotted in FIG. 12. With the exception of the adhesive formulations containing a 5% by weight dextran solution, the dendrimer-containing adhesive formulations had a higher maximum load.

Example 6

Comparison of Adhesive Formulations Containing Dendrimers With Those Containing PEG Amine of Different Molecular Weights In Example 5, the dendrimer component was a dendrimer with primary amines on 25% of its surface groups instead of hydroxyl groups, and a molecular weight of 30 kDalton. In contrast, the PEG-amine used in the other adhesive formulations of Example 5 had a molecular weight of 10 kDalton. To test the effects of the molecular weight of the PEG amine, a series of adhesives containing PEG-amines with different molecular weights were produced. Although the molecular weights differed, each adhesive contained the same number of PEG amine molecules.

Specifically, three different PEG amine components were used to formulate fifteen adhesives by combining the three PEG amine components with dextran solutions having concentrations of 5, 7.5, 10, 15, and 25% by weight. The three different PEG amine components each had eight arms (P8) and consisted of a 6.67% by weight solution of a 10 kDalton PEG-amine, a 13.34% by weight solution of a 20 kDalton PEG amine, and a 26.68% by weight solution of a 40 kDalton PEG amine.

Figure 13:
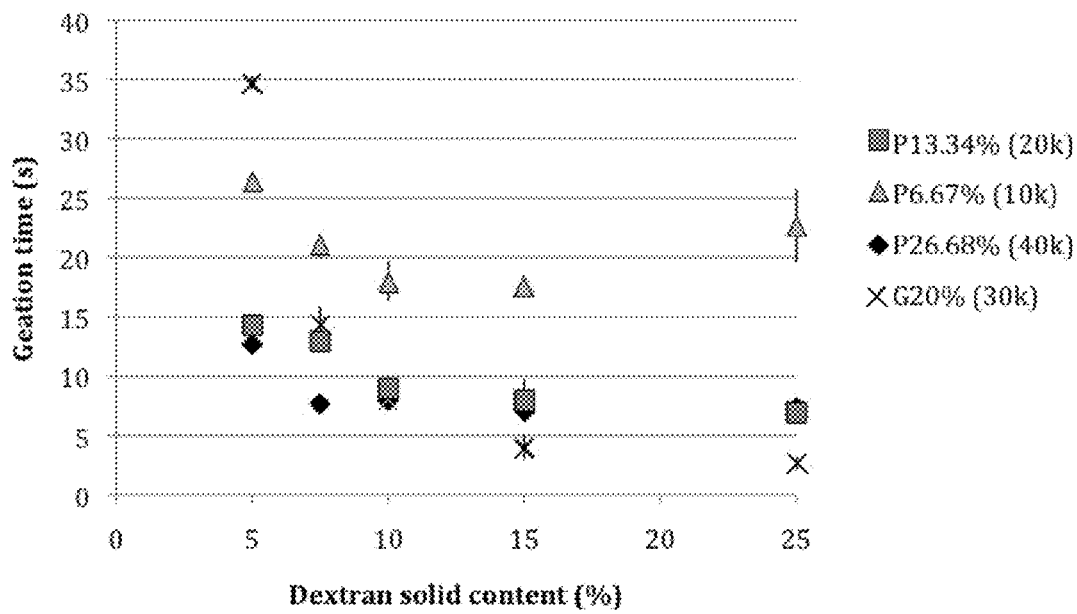
FIG. 13 depicts the gelation times of PEG amine adhesives of various molecular weights and dendrimer containing adhesive formulations.

FIG. 13 depicts the gelation times of these fifteen adhesives along with the gelation times for adhesive formulations made by combining each dextran solution with a 20% solution of a 30 kDalton G5 dendrimer having primary amines on 25% of its surface groups instead of hydroxyl groups. As the molecular weight of the PEG in the PEG amine adhesive increased, the gelation time of the PEG amine adhesive became more similar to the dendrimer-containing adhesive formulations described herein. The 20 kDalton and 40 kDalton PEG amine adhesives had approximately the same gelation times, which were less than the gelation time for the 10 kDalton PEG amine. Not wishing to be bound by any particular theory, this difference is believed to be caused by the differences in steric hindrance: the PEG amines with higher molecular weights are less sterically hindered and, as a result, more likely to react with the other component.

Figure 14:
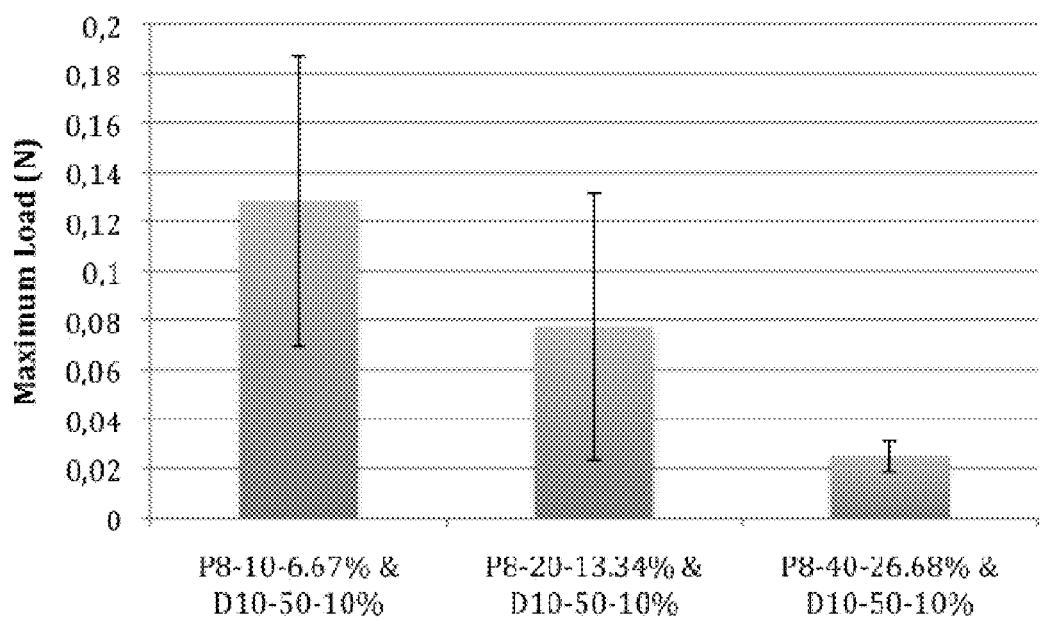
FIG. 14 depicts the tensile test results for PEG amine adhesives made with PEG amines of different molecular weights.

Although the 20 kDalton and 40 kDalton PEG amine adhesives had faster gelling times than the 10 kDalton PEG amine adhesive, the maximum load handled by the 10 kDalton PEG amine adhesive was higher than maximum loads of the 20 kDalton and 40 kDalton PEG amine adhesives. Not wishing to be bound by any particular theory, this may be related to the competition in the reaction between the aldehydes in the dextran with the amines in the tissue and the amines in the PEG amine. FIG. 14 depicts these results.

Example 7

Disease Model—Colitis Induction

A disease model was designed based on colitis. To develop the model, the differences in amine density of healthy and diseased colon was studied. The experiments indicated whether the surface of the tissue was modified by inducing inflammation, and to what extent it affected adhesion and cohesion strengths of the dendrimer-containing adhesive formulation.

For the diseased model, dinitrobenzene sulfonic acid (DNBS) was instilled at a concentration of 80 mg/mL. After 24 hours, the rabbits were euthanized and the colon was harvested, cleaned, and incubated for 20 minutes in a 0.5% aldehyde coated microspheres solution. The tissues were frozen, cryo-sectioned, and stained with propidium iodide. The intensity of the microspheres was quantified by fluorescence microscopy.

Figure 15:
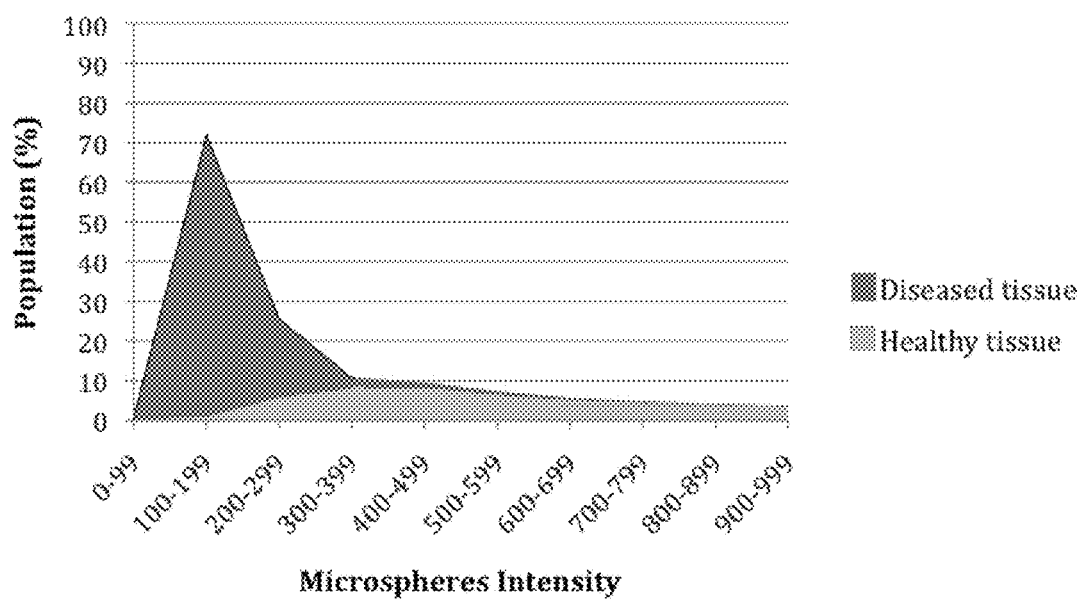
FIG. 15 depicts the distribution of the intensity of the microspheres in healthy and diseased models.
Figure 16:
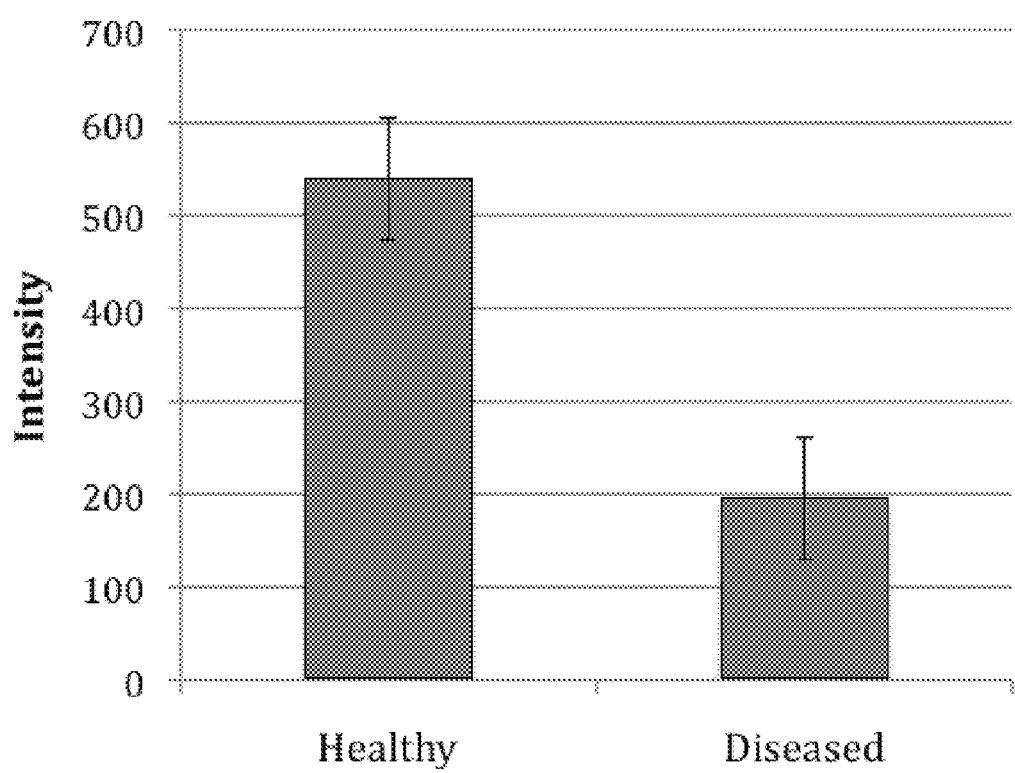
FIG. 16 depicts the average intensity of the microspheres applied to healthy and diseased tissues.

Fluorescence microscope images showed that the healthy model had a higher amine density and higher distribution along the surface. Hematoxylin and eosin stains (H & E) of the cryosectioned healthy and diseased tissues demonstrated alteration in the morphology of the luminal surface, as evidenced by hyperplasia and thickening of the colon with cell infiltrates. Serosal layer chemistry was impacted as well, as evidenced by alteration of the f-MS intensity and continuity throughout the colon in the diseased state, i.e., there were less amine groups present at the surface. FIG. 15 shows the distribution of the microsphere's intensity in the healthy and diseased models. FIG. 16 shows the average intensity of the microspheres applied to healthy and diseased tissues (colitis). This graph shows that the microsphere's average fluorescence intensity, and hence the adhesion of the dendrimer containing adhesive formulations to the tissue, dramatically dropped (over 60%) when the tissue was inflamed.

Figure 17:
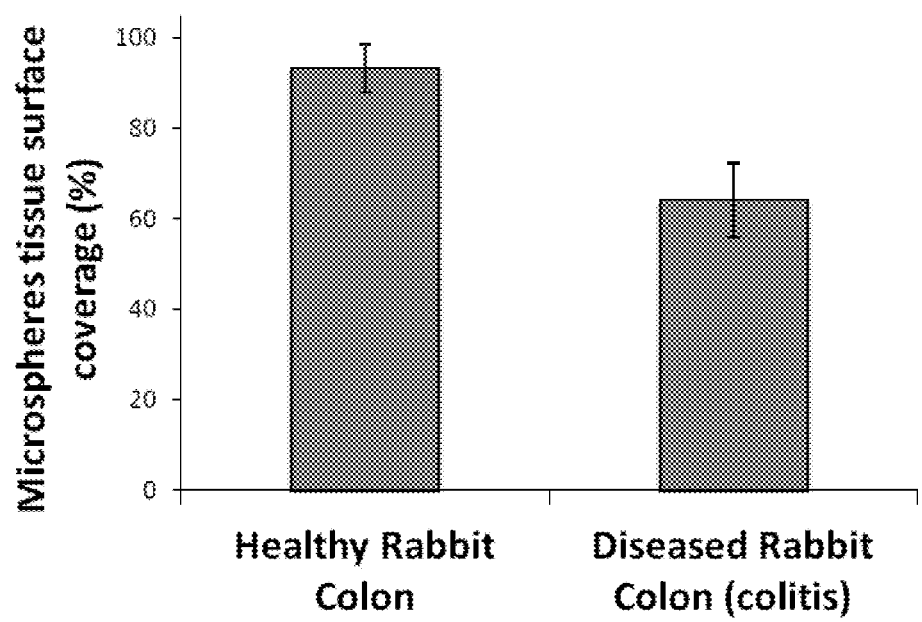
FIGS. 17 and 18 depicts the tissue surface coverage of fluorescent microspheres in healthy and diseased colon tissue.

In this model, the reduction in amine density affected the interaction between the tissue and adhesive formulation, and adhesion strength. More specifically, in this particular example, colitis resulted in lower f-MS conjugation to tissues, as evidenced by lower fluorescence intensity at the tissue surface and lower surface coverage, as shown in FIG. 17. The lower surface coverage, in this example, occurred in isolated areas and perturbed the continuous surface coverage observed in the healthy state. Therefore, the concentrations of the component solutions or the amounts of the components administered may be adjusted to compensate for this characteristic of diseased tissue. Specific material formulations can be designed to address the disease-induced alteration of tissue surface chemistry. Specifically, in certain embodiments, a formulation containing a higher amount or concentration of polymer component can be administered to compensate for the decreased number of amines on the surface of diseased tissue, thereby improving the reaction yield, improving adhesion, or both.

Example 8

Disease Model—Cancer

Figure 18:
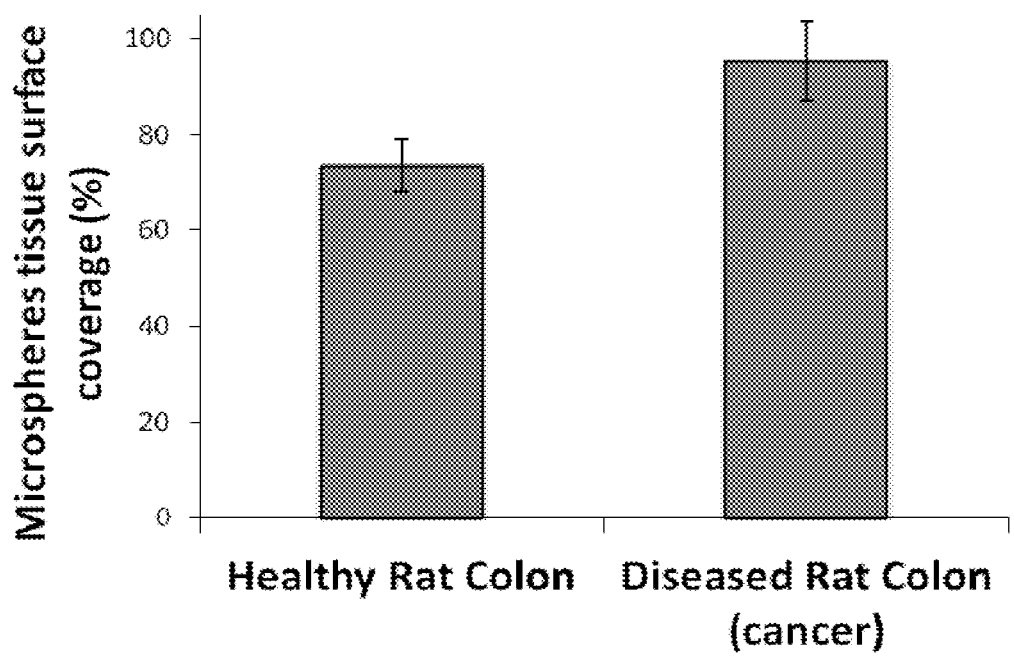
Figure 19:
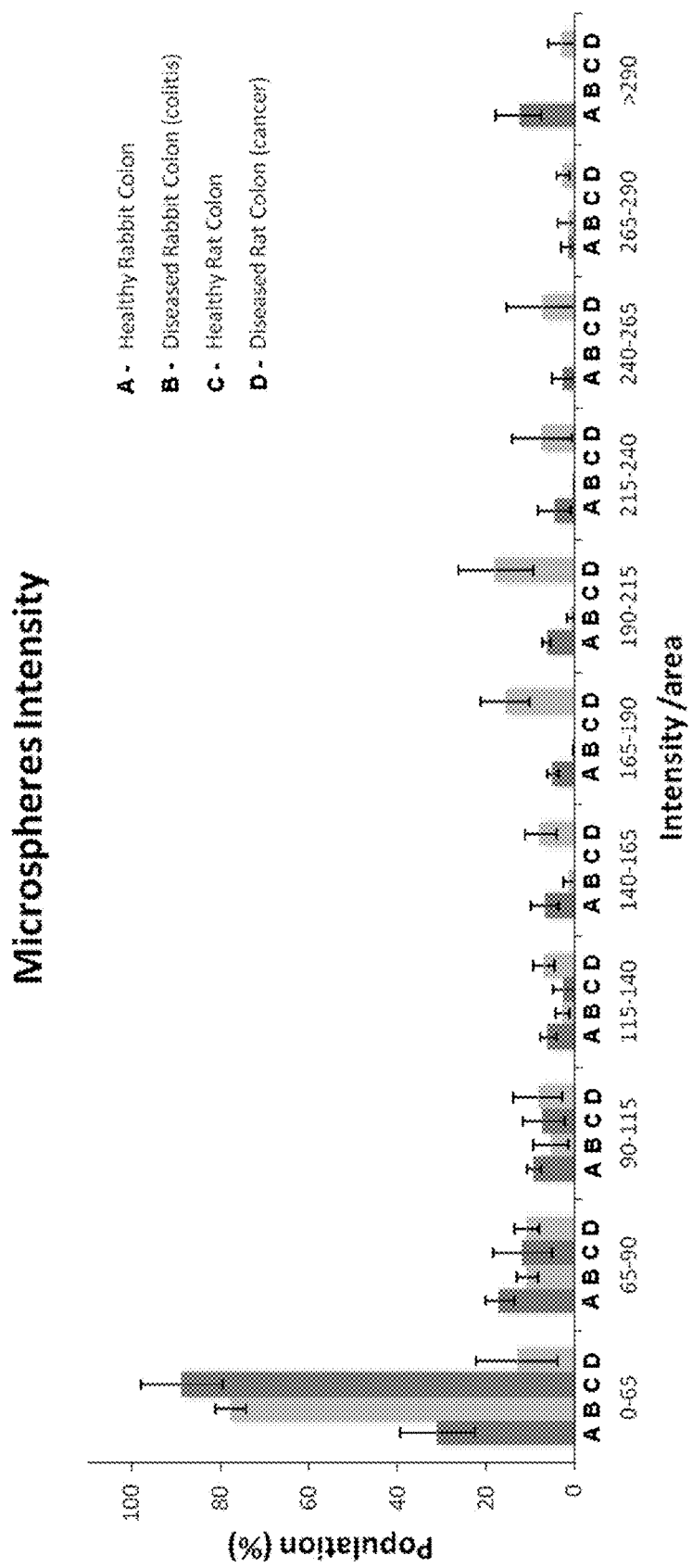
FIG. 19 depicts the fluorescent microspheres' intensity in healthy rabbit colon, diseased rabbit colon, healthy rat colon, and diseased rat colon.

The analyses in Example 7 also were performed on cancerous tissue from the colon of rats. In the cancer model, the diseased tissue had a higher f-MS tissue surface coverage than the healthy tissue, as shown in FIG. 18. The opposite results produced by the colitis model (Example 7) and the cancer model indicated the importance of tuning the adhesive formulation as described herein to compensate for disease-induced tissue alteration. A more thorough comparison of the f-MS intensity differences in the colitis model (Example 7) and the cancer model is shown in FIG. 19. FIG. 19 shows that the inflamed colon tissue from the colitis model (Example 7) had a lower tissue surface coverage of f-MS compared to the cancerous tissue in the cancer model.

Example 9

Tissue Response to Adhesive Formulation—Colitis Model

The overall tissue response to an adhesive formulation was determined by collecting a series of histology scores that indicated the severity of inflammation, serosal heterophils (at the interface with the material indicating response to the material), and serosal fibrosis (which indicates healing). The adhesive formulation used in this example included D10-50-15 and G5-25-20. The histology scores were collected for the 6 colon tissue groups listed in Table 1. In each of the groups containing incisions, the incisions were sutured. Photomicrographs of H & E stained sections were also collected, and explained in Table 1. The tissue samples were collected in a manner similar to the process of Example 7.

TABLE 1

Colon Tissue Groups

| Group No. | Description | Photomicrograph |
|---|---|---|
| I | Healthy control group - no incision, no adhesive formulation | Colon appeared normal. |
| II | Colitis control group - no incision, no adhesive formulation | Colonic mucosa was diffusely necrotic with an intense heterophilic inflammatory response. |
| III | Healthy colon - with incision, no adhesive formulation | Mild increase in the number of inflammatory cells in the mucosa; moderate heterophilic inflammatory response, predominantly in association with the suture material; mild inflammation and fibrosis was seen along serosal surface in association with the incision site/suture material. |
| IV | Colitis colon - with incision, no adhesive formulation | Colonic mucosa was diffusely necrotic with an intense heterophilic inflammatory response that extended from the mucosal surface, surrounded the suture material, and infiltrated deep to the serosal surface, where there was associated fibrosis. |
| V | Healthy colon - with incision, with adhesive formulation | Mild inflammation and fibrosis was at the interface between the serosa and adhesive material. |
| VI | Colitis colon - with incision, with adhesive formulation | A small portion of relatively normal mucosa was visible; the remainder of the colonic wall was necrotic with an intense heterophilic inflammatory response that extended from the mucosal surface, surrounded the suture material, and infiltrated deep to the serosa to surround the adhesive material. |

Figure 20:
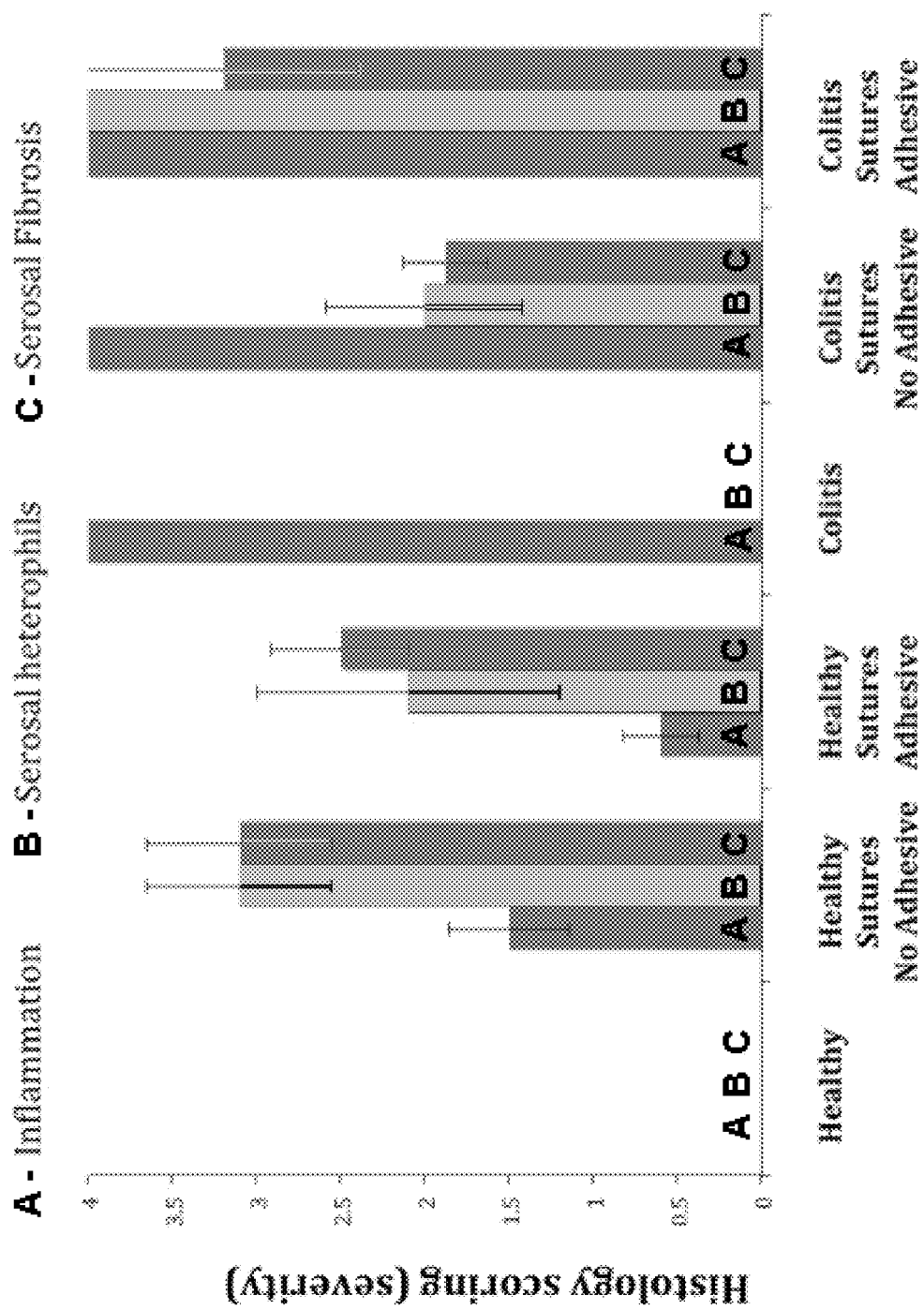
FIGS. 20 and 21 depict histology scoring for healthy and diseased tissues with and without incisions and with or without the application of an adhesive formulation.

FIG. 20 shows the histology scores collected from the tissues from Groups I-VI. In the healthy tissues (Groups I, III, and V), inflammation in Group V was less than the inflammation in Group III. Therefore, in this test, the inflammation of healthy tissues with an incision was reduced upon adhesive application. In the healthy tissues, the healing responses were similar whether or not the adhesive formulation was applied, and there was no evidence of any adverse response to the adhesive formulation.

In the diseased tissues (Groups II, IV, and V), the overall inflammation was higher than in the healthy tissues. It was observed, however, that application of the adhesive formulation increased the inflammatory response at the interface between the tissue and the adhesive formulation. Moreover, in this particular test, application of the adhesive formulation to the diseased tissues increased serosal fibrosis—i.e., enhanced healing of the tissues. Both serosal heterophils and serosal fibrosis were affected by the state of the tissue (diseased or healthy), which further demonstrated the importance, in certain instances, of tuning the adhesive formulations in view of specific microenvironmental conditions.

Example 10

Tissue Response to Adhesive Formulation—Cancer Model

The analyses in Example 9 also were performed on cancerous tissues. As in Example 9, the adhesive formulation used in this example included D10-50-15 and G5-25-20. The overall tissue response to the adhesive formulation was determined by collecting a series of histology scores that indicated the severity of inflammation, serosal heterophils (at the interface with the material indicating response to the material), and serosal fibrosis (which indicates healing). The histology scores were collected for the 6 tissue groups listed in Table 2. In each of the groups containing incisions, the incisions were sutured. Photomicrographs of H & E stained sections were also collected, and explained in Table 2. The tissue samples were collected in a manner similar to the process of Example 8.

TABLE 2

Cancer Tissue Groups

| Group No. | Description | Photomicrograph |
|---|---|---|
| VII. | Healthy control group - no incision, no adhesive formulation | Colon appeared normal. |
| VIII. | Cancer control group - no incision, no adhesive formulation | Dysplastic epithelium, characterized by nuclear crowding and hyperchromatism, indicated tumor site. |
| IX. | Healthy colon - with incision, no adhesive formulation | Mild increase in the number of inflammatory cells in the mucosa; mild inflammation and fibrosis was seen along the serosal surface in association with the incision site/suture material. |
| X. | Cancer colon - with incision, no adhesive formulation | Colonic mucosa showed a heterophilic inflammatory response surrounding the suture material, and infiltrates to the serosal surface, where there was associated fibrosis. |
| XI. | Healthy colon - with incision, with adhesive formulation | Coalescing mucosal inflammation and fibrosis at the interface between the serosa and adhesive material was observed, especially next to the suture material. |
| XII. | Cancer colon - with incision, with adhesive formulation | A small portion of relatively normal mucosa was visible, nuclear crowding showed tumor formation; the remainder of the colonic wall showed a mixture of neutrophilic inflammatory response and fibrous tissue. |

Figure 21:
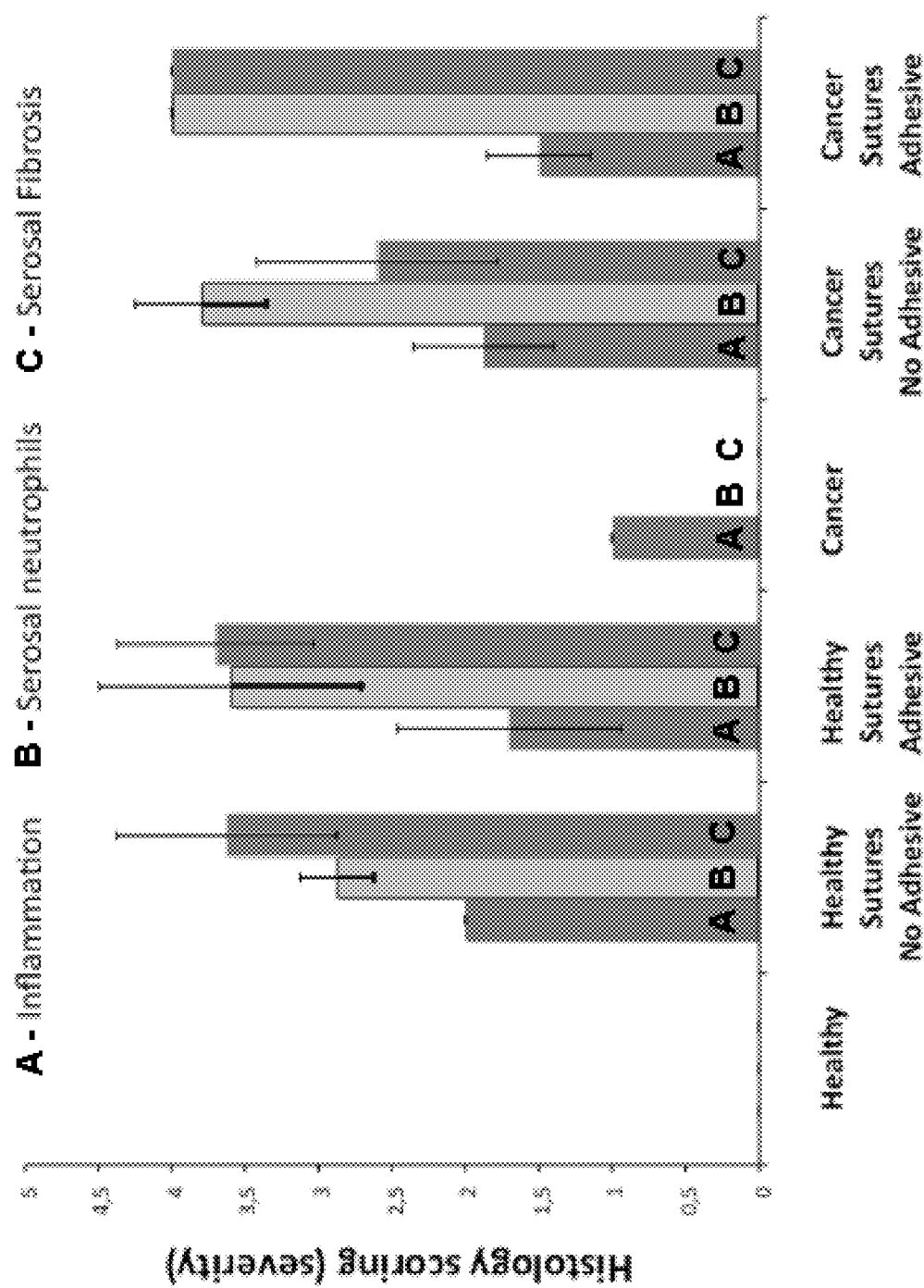

FIG. 21 shows the histology scores collected from the tissues from Groups VII-XII. The overall inflammation and surface inflammation were similar in healthy (Groups VII, IX, and XI) and diseased (Groups VIII, X, and XII) states. Similar to the colitis model (Example 8), the addition of adhesive formulation imparted healing in the cancerous tissues, as demonstrated by the elevation of surface heterophils.

We claim:

1. A kit for making an adhesive comprising:
a first part which includes a first solution comprising a polymer component, wherein the polymer component comprises a polymer having one or more aldehyde groups; and
a second part which includes a second solution comprising a dendrimer component, wherein the dendrimer component comprises a dendrimer having at least 2 branches with one or more surface groups, wherein less than 75% of the surface groups comprise at least one primary or secondary amine.

2. The kit of claim 1, further comprising a syringe, wherein the first and second solutions are stored in the syringe.

3. The kit of claim 2, wherein the syringe comprises separate reservoirs for the first solution and second solution.

4. The kit of claim 3, wherein the syringe comprises a mixing tip.

5. The kit of claim 1, further comprising at least two reservoirs with different concentrations of the first solution.

6. The kit of claim 1, further comprising at least two reservoirs with different concentrations of the second solution.

7. The kit of claim 1, further comprising instructions for selecting an appropriate concentration of at least one of the first solution or second solution to compensate for the characteristics of one or more biological tissues.

8. The kit of claim 1, wherein the dendrimer component, polymer component, or both components, comprise a drug.

9. The kit of claim 1, wherein the dendrimer component, polymer component, or both components, comprise stem cells or other cells.

10. A drug delivery composition comprising:
a polymer component, wherein the polymer component comprises a polymer having one or more aldehyde groups;
a dendrimer component, wherein the dendrimer component comprises a dendrimer having at least 2 branches with one or more surface groups, wherein less than 75% of the surface groups comprise at least one primary or secondary amine; and
at least one drug combined with at least one of the polymer component and dendrimer component.

11. The composition of claim 10, wherein the polymer and dendrimer components are in a combination effective for the composition to adhere to a biological tissue.

* * * * *